(12) United States Patent
Moscow et al.

(10) Patent No.: US 8,663,632 B1
(45) Date of Patent: Mar. 4, 2014

(54) COMPOSITIONS AND METHODS FOR SELECTIVELY TARGETING CANCER CELLS USING A THIAMINASE COMPOUND

(75) Inventors: Jeffrey Moscow, Lexington, KY (US); Shuqian Liu, Lexington, KY (US); Younsoo Bae, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 13/274,049

(22) Filed: Oct. 14, 2011

Related U.S. Application Data

(63) Continuation-in-part of application No. 12/404,004, filed on Mar. 13, 2009, now abandoned.

(60) Provisional application No. 61/393,705, filed on Oct. 15, 2010, provisional application No. 61/036,249, filed on Mar. 13, 2008.

(51) Int. Cl.
*A61K 38/46* (2006.01)
*C12N 9/14* (2006.01)

(52) U.S. Cl.
USPC .......................................... 424/94.6; 435/195

(58) Field of Classification Search
None
See application file for complete search history.

(56) References Cited

U.S. PATENT DOCUMENTS

| | | | |
|---|---|---|---|
| 6,506,550 B1 | 1/2003 | Fulton et al. | |
| 7,736,898 B1 * | 6/2010 | Fulton et al. | 435/471 |
| 2004/0013658 A1 * | 1/2004 | Fulton et al. | 424/94.1 |
| 2006/0035981 A1 | 2/2006 | Mazzio et al. | |
| 2007/0136825 A1 | 6/2007 | Frommer et al. | |
| 2008/0234304 A1 * | 9/2008 | Gyuris et al. | 514/276 |

FOREIGN PATENT DOCUMENTS

| | | | |
|---|---|---|---|
| WO | 9902192 | 1/1999 | |
| WO | 2005051976 | 6/2005 | |
| WO | WO 2009/078586 * | 6/2009 | ........... A61K 31/426 |

OTHER PUBLICATIONS

Mekhail et al. "Paclitaxel in Cancer Therapy", Expert Op. Pharmacother., 2002, 3(6):755-66.*
Slaviero et al. "Population Pharmokinetics of Weekly Docetaxel in Patients with Advanced Cancer", British J. of Clin. Pharm., 2003, 51(1):44-53.*
Moscow, et al., U.S. Appl. No. 12/404,004, filed Mar. 13, 2009.
Liu, S., Huang, H., Lu, X., Golinski, M., Comesse, S., Watt, D., Grossman, R. B., and Moscow, J. A. Down-regulation of thiamine transporter THTR2 gene expression in breast cancer and its association with resistance to apoptosis. Mol Cancer Res, 1: 665-673, 2003.
Liu, S., Stromberg, A., Tai, H. H., and Moscow, J. A. Thiamine transporter gene expression and exogenous thiamine modulate the expression of genes involved in drug and prostaglandin metabolism in breast cancer cells. Mol Cancer Res, 2: 477-487, 2004.
Cascante, et al., "Role of Thiamin (Vitamin B-1) and Transketolase in Tumor Cell Proliferation," Nutrition and Cancer, (2000) 36(2), 150-154.
Liu, et al., "Sensitivity of Breast Cancer Cell Lines to Recombinant Thiaminase I," Cancer Chemother Pharmacol (2010) 66:171-179.
Lockman, et al., "Brain Uptake of Thiamine-Coated Nanoparticles," Journal of Controlled Release 93 (2003) 271-282.
Oyewumi, et al., "Specific Association of Thiamine-Coated Gadolinium Nanoparticles with Human Breast Cancer Cells Expressing Thiamine Transporters," (2003) Bioconjugate Chem., 14, 404-411.

* cited by examiner

*Primary Examiner* — Suzanne M Noakes
(74) *Attorney, Agent, or Firm* — Stites & Harbison PLLC; Mandy Wilson Decker

(57) ABSTRACT

Compositions and methods of treating cancer using a thiaminase compound are described. The presently-disclosed subject matter includes a method of treating cancer by administering a thiaminase compound and a thiamine-dependent enzyme inhibitor.

10 Claims, 22 Drawing Sheets

COMPOSITIONS AND METHODS FOR SELECTIVELY TARGETING CANCER CELLS USING A THIAMINASE COMPOUND

RELATED APPLICATIONS

This application claims priority from U.S. Provisional Application Ser. No. 61/393,705 filed Oct. 15, 2010, and is a continuation-in-part of commonly assigned and U.S. patent application Ser. No. 12/404,004 filed Mar. 13, 2009 now abandoned, which claims priority from U.S. Provisional Application Ser. No. 61/036,249 filed Mar. 13, 2008, the entire disclosures of each of which are incorporated herein by this reference.

TECHNICAL FIELD

The presently-disclosed subject matter relates to compositions and methods of treating cancer using a thiaminase compound. In particular, the presently-disclosed subject matter relates to a method of treating cancer by administering a thiaminase compound and a thiamine-dependent enzyme inhibitor.

INTRODUCTION

Thiamine is a vitamin that plays a crucial role in the cellular energy metabolism that occurs in normal, healthy cells. The thiamine-dependent oxidative decarboxylation of pyruvate, in the aerobic metabolism of glucose, turns pyruvate into the key intermediate acetyl coenzyme A. This reaction leads to the efficient conversion of the calories in glucose into adenosine triphosphate (ATP), the fuel of cellular energy, through a set of reactions known as the tricarboxylic acid (TCA) cycle. In the absence of thiamine, glucose-derived pyruvate is turned into lactate. Additionally, thiamine is a cofactor of transketolase, a critical enzyme in the pentose phosphate pathway that produces ribose, a required constituent for DNA synthesis, and NADPH, a cofactor for multiple intracellular metabolic pathways including steroid synthesis and drug detoxification.

Unlike normal cells, cancer cells have altered energy metabolism involving thiamine-dependent pathways that preferentially shunt glucose into anaerobic glycolysis under aerobic conditions. Instead of entering the tricarboxylic acid cycle (TCA) through the thiamine-dependent pyruvate dehydrogenase (PDH) pathway, pyruvate is converted to lactate and exported unused from the cell. This observation, known as the Warburg effect, may reflect the untethering of malignant cells from growth regulation signals and may represent an important step in transformation.

Thiamine is also a required cofactor for the alpha ketoglutarate dehydrogenase enzyme complex within the TCA cycle, and for the enzyme transketolase, a key metabolic entry point into the pentose phosphate shunt. Cells require two specific transport proteins, THTR1 and THTR2, for thiamine uptake. The present inventors have shown that RNA levels of THTR1 and THTR2 are down-regulated in tumors and have contemplated that the down-regulation of thiamine uptake may make tumor cells more sensitive to thiamine starvation.

Cancer remains a prevalent condition that is responsible for many deaths each year. Accordingly, there remains a need in the art for new compositions and methods useful for treating cancer. In particular, there remains a need in the art for new compositions and methods for treating cancer that therapeutically exploit the metabolic and nutritional vulnerabilities of tumors.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter includes methods, kits, and compositions useful for treating cancer, which make use of a thiaminase compound.

A thiaminase compound can be a thiaminase enzyme, a thiaminase enzyme modified with a lipophilic moiety, a thiaminase enzyme encapsulated in a lipophilic carrier, or a thiaminase enzyme modified with a lipophilic moiety and encapsulated in a lipophilic carrier. The lipophilic moiety can be, for example, a hydrophobic moiety. The lipophilic carrier can be, for example, a micelle. The thiaminase enzyme can be, for example, a native thiaminase I or a native thiaminase II. In some embodiments, the thiaminase enzyme can be a native thiaminase I is from *Bacillus thiamineolyticus*.

A method for treating cancer as disclosed herein includes administering to a subject in need thereof an effective amount of a thiaminase compound, and administering to the subject an effective amount of a thiamine-dependent enzyme (TDE) inhibitor. In some embodiments, the method further includes administration of an anti-cancer agent and/or radiation. In some embodiments, the thiaminase compound is administered subcutaneously, intramuscularly, or intravenously. In some embodiments, the thiaminase compound is administered prior to administration of the TDE inhibitor.

A kit is provided in accordance with the presently-disclosed subject matter, including a thiaminase compound contained in a first container; and a thiamine-dependent enzyme (TDE) inhibitor contained in a second container. In some embodiments, the kit can further include an anti-cancer agent.

The presently-disclosed subject matter further includes a composition including a thiaminase modified with a lipophilic moiety, or a thiaminase compound encapsulated in a lipophilic carrier, wherein the lipophilic moiety or carrier facilitates entry into a cell, wherein the thiaminase compound can be selected from a thiaminase or a thiaminase modified with a lipophilic moiety. In some embodiments, the presently-disclosed subject matter includes a method for treating cancer, including administering to a subject in need thereof an effective amount of such a composition.

In some embodiments, administration of the thiaminase compound in combination with the TDE inhibitor produces a synergistic effect.

In embodiments of the presently-disclosed subject matter wherein a TDE inhibitor is provided or used, the TDE inhibitor can be a thiamine antagonist. In some embodiments, the thiamine antagonist can be oxythiamine, pyrithiamine, N3'pyridyl thiamine, or thiamine thiazolone. In some embodiments, the TDE inhibitor can be a thiaminase substrate. In some embodiments, the thiaminase substrate is thiamine.

In embodiments of the presently-disclosed subject matter wherein an anti cancer agent is used, the anti-cancer agent can be selected, for example, from the group consisting of anthracyclines, antimetabolites, alkylating agents, natural products, topoisomerase inhibitors, platinum-based agents, kinase-targeted agents, therapeutic antibodies, and proteasome inhibitors. In some embodiments, the anti-cancer agent is selected from the group consisting of doxorubicin, paclitaxel, docetaxel, and estramustine.

DESCRIPTION OF EXEMPLARY EMBODIMENTS

Figure 1A:
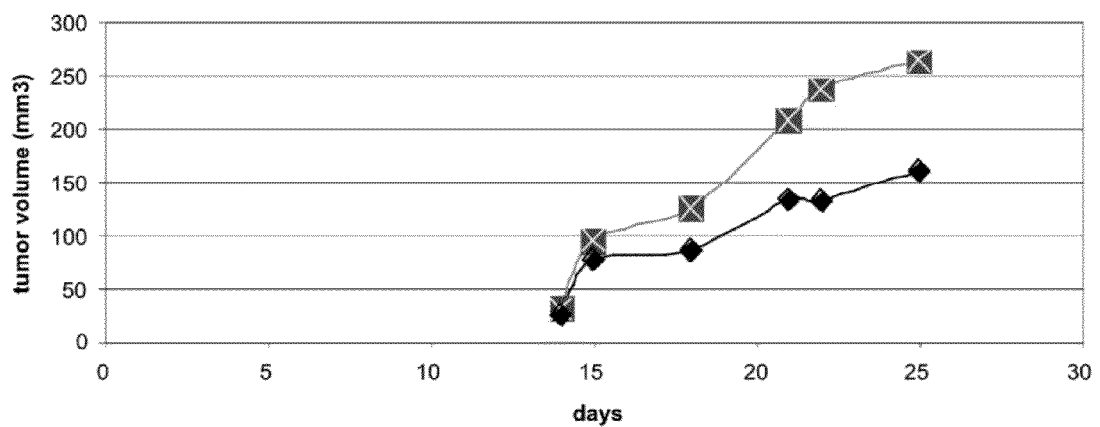
FIG. 1A is a graph showing MDA231 xenograft volume as a function of time in female nu/nu mice fed either normal chow or thiamine-deficient chow.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

Some of the polypeptide sequences disclosed herein are cross-referenced to accession numbers of publicly-accessible databases. The sequences cross-referenced in the public databases are expressly incorporated by reference as are equivalent and related sequences present in the public databases. Also expressly incorporated herein by reference are all annotations present in the public databases associated with the sequences disclosed herein. Unless otherwise indicated or apparent, the references to the public databases are references to the most recent version of the database as of the filing date of this application.

While the terms used herein are believed to be well understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The presently-disclosed subject matter includes compositions, methods, and kits for treating cancer, which include use of a thiaminase compound. The presently-disclosed subject matter further includes compositions, methods, and kits for treating cancer which include use of a thiaminase compound and a thiamine-dependent enzyme (TDE) inhibitor. In some embodiments of the presently-disclosed subject matter, a method of treating a cancer is provided, which includes administering to a subject an effective amount of a thaiminase compound. The method can further include administering an effective amount of a TDE inhibitor. In some embodiments of the presently-disclosed subject matter, a kit is provided, including a thiaminase compound and a TDE inhibitor. In some embodiments of the presently-disclosed subject matter, a composition is provided, including a thiaminase enzyme that is modified with a lipophilic moiety or which is encapsulated in a lipophilic carrier.

As used herein, the terms "treatment" or "treating" relate to any treatment of a cancer, including, but not limited to, prophylactic treatment and therapeutic treatment. As such, the terms "treatment" or "treating" include, but are not limited to: inhibiting the progression of a cancer; arresting or preventing a cancer or the development of a cancer; reducing the severity of a cancer; ameliorating or relieving symptoms associated with a cancer; and causing a regression of a cancer or one or more of the symptoms associated with a cancer.

The term "cancer" refers to all types of cancer or neoplasm or malignant tumors found in subjects, including leukemias, carcinomas, and sarcomas. Cancers can be primary or secondary. Examples of cancers include adrenal cortical cancer, brain cancer, bladder cancer, breast cancer (including mammary carcinoma, adenocarcinoma, lobular (small cell) carcinoma, intraductal carcinoma, medullary breast cancer, mucinous breast cancer, tubular breast cancer, papillary breast cancer, Paget's disease, inflammatory breast cancer, and hormone dependent tumors of the breast), cervical cancer, central nervous system (CNS) cancer, colon cancer, endometrial cancer, esophageal cancer, genitourinary tract cancer, head and neck cancer, Hodgkin's disease, kidney cancer, liver cancer, lung cancer (including small cell lung carcinomas, and non-small cell lung cancer, including squamous cell lung carcinomas, adenocarcinomas, bronchioalveolar carcinomas, adenosquamous carcinomas, papillary adenocarcinomas, mucoepidermoid carcinomas, adenoid cystic carcinomas, large cell carcinomas, and giant cell and spindle cell carcinomas), malignant carcinoid, malignant hypercalcemia, malignant pancreatic insulanoma, melanoma, mesothelioma, multiple myeloma, neuroblastoma, ovarian cancer, pancreatic cancer, macroglobulinemia, thrombocytosis, prostate cancer, renal cancer, rhabdomyosarcoma, stomach cancer, testicular cancer, thyroid cancer, uterine cancer, and medulloblastoma.

By "leukemia" is meant broadly progressive, malignant diseases of the blood-forming organs and is generally characterized by a distorted proliferation and development of leukocytes and their precursors in the blood and bone marrow. Leukemia diseases include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

The term "carcinoma" refers to a malignant new growth made up of epithelial cells tending to infiltrate the surrounding tissues and give rise to metastases. Exemplary carcinomas include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiennoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, naspharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrmcous carcinoma, and carcinoma villosum.

The term "sarcoma" generally refers to a tumor which is made up of a substance like the embryonic connective tissue and is generally composed of closely packed cells embedded in a fibrillar or homogeneous substance. Sarcomas include, for example, chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilns' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphomas (e.g., Non-Hodgkin Lymphoma), immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

As used herein, the term "subject" includes both human and animal subjects. Thus, veterinary therapeutic uses are provided in accordance with the presently-disclosed subject matter. As such, the presently-disclosed subject matter provides for the treatment of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

The methods, compositions, and kits of the presently-disclosed subject matter make use of a thiaminase compound for the treatment of a cancer in a subject. As used herein, the term "thiaminase compound" refers to a thiaminase enzyme, or a thiaminase enzyme that has been modified to enhance its ability to enter a cell. For example, such a modification can be a modification with a lipophilic moiety or encapsulation in a lipophilic carrier. As noted hereinabove, the present inventors made surprising discoveries regarding entry of thiaminase into cancer cell to affect the cells, and further surprising discoveries regarding a decreased efficacy of 5 kDa PEG-modified thiamianse as compared to un-modified thiaminase.

As such, there would have been no reason heretofore to modify thiaminase to enhance lipophilicity and to provide same for use in treating cancer.

Examples of lipophilic moieties can include hydrophobic moieties, as will be recognized by those skilled in the art. By way of provide some nonlimiting examples, lipophilic moieties can include short-chain fatty acids (SCFA: <6 carbons), medium-chain fatty acid (MCFA: 6-12 carbons), long-chain fatty acid (LCFA: 12-21 carbons), and potentially very long chain fatty acid (VLCFA: >22 carbons), which are either saturated or unsaturated, carbon chains, and benzene rings. The enzyme can be modified further with aliphatic and aromatic small moledules (<1,000 atoms) or polymers (Gauthier and Klok, 2010; Bernardes et al., 2010).

Examples of lipophilic carriers include, but are not limited to micelles and liposomes. As will be recognized by those skilled in the art upon study of this application, other moieties and/or carriers to enhance lipophilicity of the thiaminase to facilitate entry into a cell could be selected and used. By way of provide some nonlimiting examples, the thiaminase compound could be entrapped in pharmaceutically engineered nanoscale carriers, as will be recognized by those skilled in the art; such carriers can include self-assembling block copolymer micelles with charged moieties (Lee, et al., 2007) or liophilic chains (Diezi, et al., 2010).

A "thiaminase enzyme" or a "thiamianse," as used herein, refers to a polypeptide that is a thiamine-cleaving enzyme. The molecule can have an amino acid sequence of a naturally-occurring thiamine-cleaving enzyme. The thiaminase can be "isolated". The term "isolated", when used in the context of an isolated amino acid or polypeptide, is a molecule that, by the hand of man, exists apart from its native environment and is therefore not a product of nature. An isolated polypeptide can exist in a purified form or can exist in a non-native environment. Naturally-occurring thiaminases can include, but are not limited to, bacterial thiaminases, animal thiaminases (e.g., fish, silkworm), and plant thiaminases (e.g., fern). In some embodiments of the presently-disclosed subject matter, the thiaminase is a thiaminase I. In some embodiments, the thiaminase is a thiaminase II. In some embodiments, the thiaminase has an amino acid sequence of *Bacillus thiaminolyticus* thiaminase I. In some embodiments, the thiaminase is a polypeptide of a UniProt/Swiss-Prot Accession Number selected from the following: P45741, P25052, Q2FF32, Q2FWG0, Q2YUL0, Q5HEA5, Q99SG3, Q7A4F3, Q6GEY1, Q6G7L6, Q7A0C8, O54496, Q5HMC7, Q8CNK1, Q4L7x6, Q49Z42, P46351, A2FRE7, A3NJN5, A3P596, A4G3K6, A5 HZW3, A7FS27, A7 GBG8, A8ELP5, A8FC11, A8FJ01, A8KRL3, A8KS96, A8NHM0, A8VTG6, A9HL70, B0FJ10, B1H6T1, B11F93, B1 KWX1, B1Q6P2, B1QLU4, B6ERB3, B7CES6, B7GVB9, Q2T5P7, or Q3JMI6.

The thiaminase can also be provided in the form of a pharmaceutically-acceptable salt or solvate. In this regard, the term "thiaminase" is inclusive of salts and solvates of the thiaminase. A salt can be formed using a suitable acid and/or a suitable base. Suitable acids that are capable of forming salts with the compounds of the presently-disclosed subject matter include inorganic acids such as trifluoroacetic acid (TFA), hydrochloric acid (HCl), hydrobromic acid, perchloric acid, nitric acid, thiocyanic acid, sulfuric acid, phosphoric acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid, or the like. Suitable bases capable of forming salts with the compounds of the presently-disclosed subject matter include inorganic bases such as sodium hydroxide, ammonium hydroxide, potassium hydroxide and the like; and organic bases such as mono-di- and tri-alkyl and aryl amines (e.g. triethylamine, diisopropyl amine, methyl amine, dimethyl amine, and the like), and optionally substituted ethanolamines (e.g. ethanolamine, diethanolamine, and the like).

As used herein, the term "solvate" means a complex or aggregate formed by one or more molecules of a solute, e.g. a thiaminase or a pharmaceutically-acceptable salt thereof, and one or more molecules of a solvent. Such solvates are typically crystalline solids having a substantially fixed molar ratio of solute and solvent. Representative solvents include, but are not limited to, water, methanol, ethanol, isopropanol, acetic acid, and the like. When the solvent is water, the solvate formed is a hydrate. As such, the term "pharmaceutically-acceptable salt or solvate thereof" is intended to include all permutations of salts and solvates, such as a solvate of a pharmaceutically-acceptable salt of a thiaminase.

Embodiments of the methods, compositions, and kits of the presently-disclosed subject matter make use of a thiamine-dependent enzyme (TDE) inhibitor, in addition to a thiaminase compound, for the treatment of a cancer in a subject. As used herein, the term "thiamine-dependent enzyme inhibitor" or "TDE inhibitor" refers to a compound that is an antagonist of a thiamine-dependent enzyme. In some embodiments, the TDE inhibitor can be modified to enhance lipid solubility and oral bioavailablity Lipid solubility (or lipophilicity) of the enzyme can be enhanced, for example, by lipid modification techniques known to those of ordinary skill in the field of protein research. See e.g., Steinhauer, et al., 2009; Miura, et al., 2006; Porter, et al., 1996. Examples of common materials used for these modifications are glycosylphosphatidylinositol, cholesterol, and fatty acids (both saturated and unsaturated). Oral bioavailability can be enhanced, for example, either by direct modification of proteins with biocompatible polymers (i.e. poly(ethylene glycol)) or protein entrapment in drug delivery vehicles, as will be understood by those skilled in the art. See e.g., Mueller, 2010; Wadher, et al., 2009; Morishita, et al., 2006.

Thiamine-dependent enzymes include pyrovate dehydrogenase, alpha-ketoglutarate dehydrogenase, and transketolase. In some embodiments the TDE inhibitor can be a thiamine antagonist. In some embodiments, the thiamine antagonist can be oxythiamine, pyrithiamine, N3' pyridyl thiamine, or thiamine thiazolone. In some embodiments, TDE inhibitor can be a compound as described in Thomas, et al., 2008, which is incorporated herein by this reference. In some embodiments, the TDE inhibitor can be a thiaminase substrate. In some embodiments the thiamianse substrate can be thiamine. In some embodiments, the TDE inhibitor can be a compound described in Huerou, et al., 2007, which is incorporated herein by this reference.

In this regard, the presently-disclosed subject matter includes a method for treating cancer, including administering to a subject in need thereof an effective amount of a thiaminase compound, and administering to the subject an effective amount of a TDE inhibitor, such as a thiamine antagonist. The presently-disclosed subject matter further includes a method for treating cancer, including administering to a subject in need thereof an effective amount of a thiaminase compound, and administering to the subject an effective amount of a TDE inhibitor, such as a thiaminase substrate.

It had previously been believed that thiamine starvation was toxic to all cells. As such, a cell experiencing thiamine starvation achieved by administration of thiaminase was thought to be capable of rescue by administration of thiamine. Quite distinctly, the present inventors surprisingly and unexpectedly discovered that a thiaminase compound has greater toxicity when administered with thiamine than without thiamine.

In some embodiments, methods, compositions, and kits of the presently-disclosed subject matter include providing and/or administering a thiaminase compound, or a thiaminase compound and a TDE inhibitor, in combination with an anti-cancer agent. As used herein, the term "anti-cancer agent" refers to an agent that is capable of affecting a treatment as defined herein. For example, the anti-cancer agent may kill cancer cells, induce apoptosis in cancer cells, reduce the growth rate of cancer cells, reduce the incidence or number of metastases, reduce tumor size, inhibit tumor growth, reduce the blood supply to a tumor or cancer cells, promote an immune response against cancer cells or a tumor, prevent or inhibit the progression of cancer, or increase the lifespan of a subject with cancer.

Examples of anti-cancer agents include, but are not limited to, platinum coordination compounds such as cisplatin, carboplatin, or oxalyplatin; taxane compounds, such as paclitaxel or docetaxel; topoisomerase I inhibitors, such as camptothecin compounds for example irinotecan or topotecan; topoisomerase II inhibitors, such as anti-tumor podophyllotoxin derivatives for example etoposide or teniposide; anti-tumor vinca alkaloids for example vinblastine, vincristine or vinorelbine; anti-tumor nucleoside derivatives for example 5-fluorouracil, gemcitabine or capecitabine; alkylating agents, such as nitrogen mustard or nitrosourea for example cyclophosphamide, chlorambucil, carmustine or lomustine; anti-tumor anthracycline derivatives for example daunorubicin, doxorubicin, idarubicin or mitoxantrone; HER2 antibodies for example trastuzumab; estrogen receptor antagonists or selective estrogen receptor modulators for example tamoxifen, toremifene, droloxifene, faslodex or raloxifene; aromatase inhibitors, such as exemestane, anastrozole, letrazole and vorozole; differentiating agents, such as retinoids, vitamin D and retinoic acid metabolism blocking agents (RAMBA) for example accutane; DNA methyl transferase inhibitors for example azacytidine; kinase inhibitors for example flavoperidol, imatinib mesylate or gefitinib; farnesyltransferase inhibitors; HDAC inhibitors; other inhibitors of the ubiquitin-proteasome pathway for example Velcade; or Yondelis; or estrogen derivatives, such as estramustine. As will be apparent to those skilled in the art, the particular anti-cancer agent that is selected can vary, depending on the particular cancer being treated.

In some embodiments, methods, compositions, and kits of the presently-disclosed subject matter include providing and/or administering a thiaminase compound, or a thiaminase compound and a TDE inhibitor, in combination with radiation. The term "radiation", as used herein, refers to any radiation that may be used in cancer treatment to control cancer cells. The radiation may be a curative, adjuvant, or palliative radiotherapy. Such radiation includes, but is not limited to, various forms of ionizing radiation, external bean radiotherapy (EBRT or XBRT) or teletherapy, brachytherapy or sealed source therapy, intraoperative radiotherapy, and unsealed source radiotherapy. In some embodiments, the radiation is ionizing radiation.

In some embodiments, the administration of a thiaminase compound and the administration of TDE inhibitor in accordance with the presently-disclosed methods produces an effect that exceeds the effect of either the thiaminase compound alone or the TDE inhibitor alone. In some embodiments, the administration of a thiaminase compound and the administration of TDE inhibitor in accordance with the presently-disclosed methods produces a synergistic effect.

In some embodiments, the administration of the combination of a thiaminase compound and an anti-cancer agent and/or the radiation produces an effect that exceeds the effect of either the thiaminase compound alone or the anti-cancer agent and/or the radiation alone. In some embodiments, the administration of the combination of the thiaminase compound and the anti-cancer agent and/or the radiation produces a synergistic effect.

In some embodiments, the administration of a thiaminase compound, the administration of TDE inhibitor, and the administration of an anti-cancer agent and/or the radiation in accordance with the presently-disclosed methods produces an effect that exceeds the effect of either the thiaminase compound alone, the TDE inhibitor alone, or the anti-cancer agent and/or the radiation alone. In some embodiments, the administration of a thiaminase compound, the administration of TDE inhibitor, and the administration of an anti-cancer agent and/or the radiation in accordance with the presently-disclosed methods produces a synergistic effect.

As used herein, "synergy" or "synergistic effect" can refer to any substantial enhancement, seen with the administration of a thiaminase compound in combination with a TDE inhibitors, an anti-cancer agent and/or radiation, of a measurable effect, e.g. a cancer cell killing or growth inhibition effect, when compared with the effect of a thiaminase alone, a TDE inhibitor alone, an anti-cancer agent alone and/or the radiation alone. Synergy is a specific feature of the presently-disclosed subject matter, and is above any background level of enhancement that would be due solely to, for example, additive effects.

In some embodiments, a substantial enhancement of a measurable effect can be expressed as a combination index (CI). CI can be calculated for each combination of thiaminase and anti-cancer agent using, for example Calcusyn software (Biosoft, Cambridge, United Kingdom), which performs calculations and quantifies synergy using the Median Effect methods described by T-C Chou and P. Talalay (Trends Pharmacol. Sci. 4, 450-454), which is incorporated herein by this reference. In some embodiments, a substantial enhancement of a measurable effect is found when CI, calculated using CalcuSyn Version 2.0, is less than about 1. In some embodiments, a substantial enhancement of a measurable effect is found when CI is less than about 0.99, 0.95, 0.90, 0.85, 0.80, 0.75, 0.70, or 0.65.

The term "in combination with", when used herein to describe administering a thiaminase compound, a TDE inhibitor, an anti-cancer agent and/or radiation refers to administering a thiaminase compound to a subject and administering a TDE inhibitor, an anti-cancer agent and/or radiation to the subject. In different embodiments of the presently-disclosed subject matter, the thiaminase compound, the TDE inhibitor, the anti-cancer agent and/or radiation can be administered in any order, or concurrently.

Although the thiaminase compound can be administered before, concurrently with, or after administration of the TDE inhibitor, in some embodiments it can be desirable to administer the thiaminase compound before the TDE inhibitor. In this regard, prior administration of the thiaminase can be used to create a thiamine starvation state; and then when the TDE inhibitor is administered, TDE apoenzymes can more readily bind to the TDE inhibitor.

As noted herein, in some embodiments the TDE inhibitor is a thiaminase substrate and in other embodiments the TDE inhibitor is not a thiaminase substrate. Depending on the type of TDE inhibitor that is selected for use, it may be useful to select different administration protocols. For example, in some embodiments, a thiaminase compound is administered for two days, after which a TDE inhibitor that is not a thiaminase substrate could be administered, and then both could be administered concurrently on subsequent treatment days. On the other hand, if a TDE inhibitor is selected that is a thiaminase substrate it can be desirable to delay administration until after clearance of the thiaminase compound.

In some embodiments, the thiaminase compound is administered before the anti-cancer agent and/or the radiation is administered. In some embodiments, the thiaminase compound is administered after the anti-cancer agent and/or the radiation is administered. In some embodiments, the thiaminase compound and the anti-cancer agent and/or the radiation are administered concurrently.

In some embodiments, a thiaminase compound and an anti-cancer agent are formulated in a composition for concurrent administration. In some embodiments, the TDE inhibitor and the anti-cancer agent are formulated in a composition for concurrent administration. In some embodiments, a TDE inhibitor and a thiaminse compound are formulated in a composition for concurrent administration.

In some embodiments of the presently-disclosed subject matter, the method of treating cancer comprises selectively killing cancer cells. It had previously been believed that thiamine starvation was toxic to all cells because all cells require thiamine. As such, it was thought that, although thiamine starvation by administration of thiaminase might achieve cell death, it would not have been thought to be capable of achieving selective cell death. The present inventors have surprisingly and unexpectedly discovered that administration of a thiaminase compound in accordance with the presently-disclosed subject matter selectively targets cancer cells. As used herein, the term "selectively killing" refers to an enhanced cytotoxicity in cancer cells, as compared to other cells.

Suitable methods for administering a thiaminase compound and/or a TDE inhibitor to a subject include, but are not limited to, oral administration, systemic administration, parenteral administration (including intravenous, intramuscular, intraarterial, intratumoral, or intradermal administration), subcutaneous administration, inhalation, surgical implantation, transdermal delivery, local injection, and hyper velocity injection/bombardment. Where applicable, continuous infusion can enhance drug accumulation at a target site, if desired (see, e.g., U.S. Pat. No. 6,180,082). In some embodiments, the thiaminase compound is administered by oral, parenteral, and/or intratumoral administration.

Administration of the anti-cancer agent can be made by any appropriate means known to those of ordinary skill in the art. Administration of the radiation can be made by any appropriate means known to those of ordinary skill in the art.

For administration of a thiaminase compound and/or a TDE inhibitor, as disclosed herein, conventional methods of extrapolating human dosage based on doses administered to a murine animal model can be carried out using the conversion factor for converting the mouse dosage to human dosage: Dose Human per kg=Dose Mouse per kg×12 (Freireich et al., (1966) *Cancer Chemother Rep.* 50:219-244). Drug doses can also be given in milligrams per square meter of body surface area because this method, rather than body weight, achieves a good correlation to certain metabolic and excretionary functions. Moreover, body surface area can be used as a common denominator for drug dosage in adults and children as well as in different animal species as described by Freireich et al. (Freireich et al., (1966) *Cancer Chemother Rep.* 50:219-244). Briefly, to express a mg/kg dose in any given species as the equivalent mg/sq m dose, multiply the dose by the appropriate km factor. In an adult human, 100 mg/kg is equivalent to 100 mg/kg×37 kg/sq m=3700 mg/m².

For additional guidance regarding formulation and dose, see U.S. Pat. Nos. 5,326,902; 5,234,933; PCT International Publication No. WO 93/25521; Berkow et al., (1997) *The Merck Manual of Medical Information*, Home ed. Merck Research Laboratories, Whitehouse Station, N.J.; Goodman et al., (2006) *Goodman & Gilman's the Pharmacological Basis of Therapeutics*, 11th ed. McGraw-Hill Health Professions Division, New York; Ebadi, (1998) *CRC Desk Reference of Clinical Pharmacology*. CRC Press, Boca Raton, Fla.; Katzung, (2007) *Basic & Clinical Pharmacology*, 10th ed. Lange Medical Books/McGraw-Hill Medical Pub. Division, New York; Remington et al., (1990) *Remington's Pharmaceutical Sciences*, 18th ed. Mack Pub. Co., Easton, Pa.; Speight et al., (1997) *Avery's Drug Treatment: A Guide to the Properties, Choice, Therapeutic Use and Economic Value of Drugs in Disease Management*, 4th ed. Adis International, Auckland/Philadelphia; and Duch et al., (1998) *Toxicol. Lett.* 100-101:255-263.

The particular mode of thiaminase compound and/or TDE inhibitor administration used in accordance with the presently-disclosed subject matter depends on various factors, including but not limited to the particular thiaminase, the carrier employed, the severity of the condition to be treated, and mechanisms for metabolism or removal of the thiaminase following administration.

The term "effective amount" is used herein to refer to an amount of a thiaminase compound and/or a TDE inhibitor sufficient to produce a measurable biological response (e.g., a response indicative of a treatment, such as a reduction in the number of cancer cells). Actual dosage levels of active ingredients in a thiaminase compound composition and/or TDE inhibitor composition of the presently-disclosed subject matter can be varied so as to administer an amount of the active components that is effective to achieve the desired therapeutic response for a particular subject and/or application. The selected dosage level will depend upon a variety of factors including the activity of the therapeutic composition, formulation, route of administration, combination with other drugs or treatments, e.g., radiation, severity of the condition being treated, and the physical condition and prior medical history of the subject being treated. Preferably, a minimal dose is administered, and the dose is escalated in the absence of dose-limiting toxicity to a minimally effective amount. Determination and adjustment of a therapeutically effective dose, as well as evaluation of when and how to make such adjustments, will be apparent to those of ordinary skill in the art upon studying this document. In some embodiments of the presently-disclosed subject matter, the thiaminase compound and/or the TDE inhibitor is administered at a concentration of about 0.1, 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, or 10 units/kg.

In some embodiments of the presently-disclosed subject matter, a kit is provided. In some embodiments, the kit comprises a thiaminase compound, wherein the thiaminase compound is as described hereinabove. In some embodiments, the kit further includes a TDE inhibitor, wherein the TDE inhibitor is as described hereinabove. In some embodiments, the kit further includes a diluent. In some embodiments, the kit further includes instructions directing administration of the thiaminase compound, or the thiaminse compound and the TDE inhibitor. In some embodiments, the thiaminase compound and/or the TDE inhibitor is freeze-dried. In some embodiments, the kit further comprises an anti-cancer agent. In some embodiments the kit further comprises a device useful for administering the thiaminase compound, the TDE inhibitor, and/or anti-cancer agent, for example, a syringe.

In some embodiments, a kit is provided including instructions for administering the thiaminase compound in combination with a therapeutic selected from a TDE inhibitor, an anti-cancer agent and/or radiation such that an effect is achieved that exceeds either the effect of the thiaminase compound, the TDE inhibitor, the anti-cancer agent, or the radiation alone. In some embodiments, a kit is provided including instructions for administering the thiaminase compound in combination with the TDE inhibitor, anti-cancer agent and/or radiation such that a synergistic effect is achieved. In some embodiments, the a kit is provided including instructions for administering the thiaminase compound in combination with the TDE inhibitor, the anti-cancer agent and/or radiation to selectively kill cancer cells.

The presently-disclosed subject matter is further illustrated by the following specific but non-limiting examples. The following examples may include compilations of data that are representative of data gathered at various times during the course of development and experimentation related to the present invention.

EXAMPLES

Example 1

Since down-regulation of thiamine transporters can cause thiamine starvation adaptation in tumors, cell culture models were developed to manipulate extracellular thiamine concentrations to create thiamine starvation that could mimic thiamine transport deficiency. Since standard medium and serum contain thiamine, these studies necessitated adaptation of cancer cell lines to growth in defined medium. Once cell lines were adapted to growth in defined medium in physiologic thiamine conditions, complete thiamine starvation could be achieved by substituting identical medium lacking thiamine. Under these conditions, the adaptation of cancer cell lines to thiamine starvation were studied to determine how cellular response to thiamine starvation compares to previous models that used gene transfection and siRNA methods to vary THTR2 expression in breast and lung cancer cells.

Methods

Thiaminase I Production:

A plasmid containing the *Bacillus thiaminolyticus* thiaminase I gene was re-amplified with different ends in order to insert it into the pRSET T7 expression vector (Invitrogen, CA) which is IPTG-inducible and has an N-terminal polyhistidine tag and the Xpress™ epitope that allows detection and efficient purification of the expressed recombinant enzyme. After IPTG-induction, cells were collected and lysed, and the recombinant enzyme was purified from cytosol using a nickel affinity column (HisTrap FF column, GE Healthcare, NJ) according to the manufacturer's protocol. Thiaminase I enzyme activity was determined with a spectrophotometric assay based on a method developed by Lienhard and modified by Costello and colleagues.[5] The assay is based on a change of absorbance at 252 nm resulting from the reaction of thiamine with secondary nucleophiles.

Cell Culture Conditions:

H460 lung cancer cells, MDA231 breast cancer cells and human mammary epithelial cells (HMEC) were grown in defined medium to control the extracellular thiamine concentration. The cells were adapted to growth in custom medium M-171 (Cascade Biologics, OR) that contained 10 nM thiamine; the usual thiamine concentration in media is ≥1 µM. Since serum also contains thiamine, cells were then adapted to growth in the medium with decreasing amounts of serum, down to a minimal amount of dialyzed serum as a growth supplement (0.1%). Thiamine withdrawal was then accomplished by changing the M-171 medium containing 10 nM thiamine to thiamine-free medium.

Determination of Cellular ATP Levels:

ATP was measured by a luciferin-luciferase assay using Bioluminescent Somatic Cell Assay kit (Sigma, Mo.). According to the manufacturer's protocol, 100 µA of cell lysate was added to 100 µl of ATP assay mix solution and light emission was measured immediately with a luminometer (Monolight™ 3010, PharMingen). ATP concentrations were calculated from a calibration curve constructed for each experiment using standard ATP dissolved in the appropriate buffer in which the experiment was performed.

Western Blot Analysis of Metabolism Regulation and Caspase Cleavage after Radiation Exposure:

Protein extracted from cells harvested after thiamine status manipulation and radiation exposure were electropheresed on polyacrylamide-SDS gels and transferred to nylon membranes. The membranes were probed by standard Western blot techniques with commercially-available antibodies. The bound immune complexes were detected using a chemiluminescence method (Pierce, IL). An anti-β-actin antibody was used as a control for protein loading.

Radiation Exposure Experiments:

Cells were irradiated using a 130 kV X-ray machine (Faxitron X-ray corporation) with a dose rate of 89.7 cGy/min. For cell cycle analysis, a total of $5 \times 10^4$ cells/well were grown in 6-well plates for 24 hours and then treated with 10 Gy dose of radiation. At different time points, treated and untreated control cells were collected and fixed with ethanol for at least 2 hours. The cells were pelleted by centrifugation, and washed with PBS. The supernatant was removed and the cell pellet was resuspended in propidium iodide (PI)/Triton X-100 staining solution (20 ug/ml PI, 0.1% Triton X-100, 0.2 mg/ml RNaseA) for 15 min at 37° C. Analysis of cell cycle distribution was performed using a flow cytometer (FACS Calibur, Becton Dickinson, San Jose, Calif.).

RT-PCR Experiments:

Quantitative RT-PCR was performed using SYBR Green PCR kit (Applied Biosystems, Foster City, Calif.) on an iCycler iQ Realtime PCR Detection System (Bio-Rad, Hercules, Calif.) according to the instructions supplied by the manufacturer. Briefly, after a 10-minute hot start at 95° C., the amplification reaction proceeded through 40 cycles of 95° C. denaturation for 10 seconds, 60° C. to 64° C. annealing for 30 seconds, and 72° C. extension for 30 seconds. Normal liver cDNA and placenta cDNA (Clontech, Palo Alto, Calif.) were used as standard curves to measure 15-PDGH and CYP4B1 gene expression respectively. Human breast cancer cell line MCF-7 cDNA was used as standard curve for TFF1 and actin expression. Quantification was performed with the iCycler analysis software. Gene expression was normalized to actin, and results presented as the ratio of gene expression to actin expression.

Results

To initially explore the effects of thiamine starvation and repletion in cancer cells, the breast cancer cell line MDA231, the lung cancer cell line H460, and non-malignant human mammary epithelial cells (HMEC) were adapted to growth in defined medium in physiologic concentrations (10 nM) of thiamine. The cells were adapted to these conditions by gradual reduction of serum supplementation. Thiamine starvation was then created using two methods. First, by incubation in the defined medium, thiamine starvation was effected by simple removal of thiamine from the medium. Second, the recombinant enzyme thiaminase I was used to digest thiamine in the defined medium.

Because of the role of thiamine in the production of ATP, it was hypothesized that thiamine starvation would decrease energy generation, and should be reflected in decreased cellular ATP levels as previously described in thiamine-deprived neuroblastoma cells.[6] An initial decrease in ATP levels to approximately 40% to 60% of control levels by day 4 was seen in the MDA231 breast cancer cells, H460 lung cancer cells, and HMECs cell lines ($p \leq 0.001$ relative to control in all three cases), and near recovery of ATP levels after addition of thiamine back to the medium (repletion) was seen within 48 hours. A similar decrease in ATP levels was seen in all three cell lines incubated in the defined medium with thiaminase I enzyme for 4 days ($p<0.01$ relative to control in all three cell lines). These studies suggest that cellular ATP levels can be used to monitor acute thiamine starvation, and that thiamine starvation and thiaminase I exposure have similar effects on cellular ATP levels.

Cell cycle analyses of MDA31 cells on the 4th day of thiamine depletion showed a decrease from 33% to 25% of cells in S-phase, and HMEC cells showed a decrease from 17% to 11% of cells in S-phase. There was no difference in the number of apoptotic and necrotic cells in both cell lines over 6 days of thiamine starvation.

Surprisingly, it was observed that MDA231 and H460 cells could adapt to prolonged thiamine starvation. Even though thiamine is considered an essential vitamin, complete thiamine withdrawal does not necessarily lead to markedly decreased proliferation of these two cell lines. Analysis of ATP levels in thiamine-starved MDA231 and H460 cells shows that after a few days of low ATP levels, there was a gradual increase of ATP levels back to the baseline levels by the 10th day and 20th day, respectively, without the addition of thiamine. In contrast, HMECs cells did not show a similar adaptation to thiamine starvation. The thiamine-starved HMEC showed slower growth than the HMEC control cells (the ultimate growth arrest of HMECs did not occur during the experimental period), and thiamine-starved HMEC cells did not demonstrate spontaneous recovery of ATP levels. These observations suggest that MDA231 and H460, but not HMECs, may adapt to thiamine starvation by altering energy metabolism from thiamine-dependent to thiamine-independent pathways.

These studies demonstrate four conditions of thiamine status: A) the baseline steady state condition (or the control state) of cells grown in medium containing thiamine; B) the thiamine-starved state, achieved by MDA231, H460 cell lines and HMECs, that is characterized by low ATP levels; C) the thiamine-repleted state, which is the state of thiamine-starved cells after being refed with medium containing thiamine, and restoration of ATP levels, also achieved by the studied malignant cell lines and HMECs; and D) the adapted state, which is the steady state condition after adaptation to thiamine-depleted conditions, which was achieved by MDA231 and H460 cell lines but not by HMECs.

To explore the cellular response to thiamine starvation, the expression of proteins involved in energy metabolism was examined by Western blot. Total Akt expression in MDA231 and H460 cells showed little change, but there was a significant increase in phosphorylated Akt in H460 cells and MDA231 cells in the repleted and adapted states. These changes were not seen in HMEC. There was no change in total GSK3β in the different thiamine starvation states, but there was a significant increase in phosphorylated GSK3β in MDA231 and H460 cells in both the repleted and adapted states. Also, there was no increase in total mTOR protein levels, but an increase in phosphorylated mTOR was observed in both cancer cell lines in both the depleted, repleted and adapted states. Surprisingly, no changes were observed in total AMPK and p-AMPK in either cell line, despite documented decrease in ATP levels. Also no changes were observed in PTEN or Beclin1 protein levels in the depleted and repleted states.

HIF1 and downstream phosphorylated PDK1 also were increased in MDA231 and H460 cells adapted to thiamine-free conditions. Conversely, Bcl-2 family members, including anti-apoptotic Bcl-2 and pro-apoptotic Bax and Bad, were all down-regulated in the adapted H460 and MDA231 cells.

Previous studies have examined the effects of THTR2 expression on gene expression in ZR-75, MCF-7 and MDA231 breast cancer cell lines transfected with THTR2.[4] In these studies, RNA levels of two genes, CYP4B1 and 15-PDGH were up-regulated in association with increased THTR2 expression, and one gene TFF1 was consistently down-regulated. These associations in gene expression were also observed in tumors compared to non-malignant adjacent tissue, and in THTR2 knock-down studies.[4] These observations have posed the question of whether the effect of THTR2 expression on gene expression is due to the availability of thiamine or whether the THTR2 transport may have functions other than mediating the uptake of thiamine. It was hypothesized that increased THTR2 expression should have the opposite effect of thiamine starvation.

To compare the effects of thiamine starvation adaptation in the MDA231 cells to THTR2 gene transfection in MDA231 cells, RNA levels of CYP4B1, 15-PDGH and TFF1 were examined in the thiamine starvation-adapted cells. In both the present study and the previous study, expression of CYP4B1 was below the limit of detection in MDA231 cells. For 15-PDGH, the previous study showed a 3.5-fold increase in expression between MDA231/THTR2 cells and control cells, whereas there was no difference in 15-PDGH RNA levels between control MDA231 and thiamine starvation adapted cells. For TFF1, previous studies showed a 6.7-fold decrease in TFF1 levels between MDA231/THTR2 and control cells, and the current studies show a 52% increase in TFF1 RNA levels in the adapted cells in comparison to the control cells when normalized to actin controls ($1.1 \pm 0.3$ vs $0.72 \pm 0.05$ for adapted vs control cells, respectively, in arbitrary units).

It was also previously found that THTR2-transfected ZR-75 breast cancer cells showed increased sensitivity to ionizing radiation, which suggests that thiamine starvation from decreased THTR expression may result in resistance to radiation.[3] To directly determine whether thiamine starvation adaptation would affect radiation sensitivity in breast cancer cells, the control and thiamine starvation adapted MDA231 cells were exposed to ionizing radiation and cell number and cell cycle distribution after exposure were measured. Thiamine starvation adapted cells showed less toxicity (decrease in cell number) as a percent of control after radiation exposure than control cells, and this was associated with a less efficient S phase blockade relative to control cells after radiation exposure, where there were 22% vs 6% in S phase on day 1 and 11% vs 0% on day 2 for adapted vs control cells, respectively. This further suggests that the down-regulation of THTR2 observed in tumors, which may lead to thiamine starvation adaptation in vivo, may contribute to radiation resistance in breast tumors.

Discussion

It was hypothesized that down-regulation of the mechanism of thiamine uptake in breast and lung tumors may cause a state of thiamine deprivation in these tumors. To understand more about the consequences of thiamine deprivation in tumor cells, models of thiamine starvation in the breast cancer cell line MDA231 and the lung cancer cell line H460, and one non-malignant cell line HMEC were developed, and the cellular response to both thiamine starvation created by two methods—absolute thiamine withdrawal and incubation in medium containing the bacterial enzyme thiaminase I was examined. In addition, the adaptation of cancer cell lines to prolonged thiamine deprivation was also characterized.

Previous studies of thiamine starvation have utilized thiamine analogs, such as pyrithiamine and oxythiamine and amprolium, that both compete for uptake and may inhibit thiamine dependent enzymes.[6,7] Bettendorff and colleagues have previously reported that adaptation to physiologic (6 nM) extracellular thiamine concentration still required addition of the thiamine analog amprolium to observe a decrease ATP levels in cultured neuroblastoma cells.[6] However, uncertainty about the extent of both thiamine uptake inhibition and extent of thiamine-dependent enzyme inhibition by thiamine analogs suggested that these analogs could not definitively mimic actual and complete thiamine starvation. The cell culture model used in the present studies demonstrated decreased ATP levels without addition of thiamine antagonists.

The present studies also describe states of thiamine starvation status: the acutely depleted state, which occurs in approximately 4 days after thiamine starvation, and which is characterized by reduced ATP levels; the repleted state, which is the state achieved after rescue of depleted cells with exogenous thiamine, and the adapted state, which can be achieved by H460 and MDA231 cell lines, but not HMEC, which is characterized by the return of cellular ATP levels back to the baseline level without exogenous thiamine, and which is associated with changes in constitutive expression and phosphorylation status of proteins governing energy metabolism and cellular survival.

In the studies described herein, acute thiamine starvation in the context of a thiamine deprivation state created by the down-regulation of thiamine uptake, provides a new avenue for the therapeutic exploitation of a nutritional vulnerability, in which thiamine deprivation could be exacerbated by the administration of the enzyme thiaminase I. This therapeutic model is analogous to the use of l-asparaginase in the treatment of acute lymphoblastic leukemia (ALL). In ALL, the metabolic vulnerability of the cancer cell is the down-regulation of asparagine synthase, the essential nutrient is asparagine, and the therapeutic agent to exploit the vulnerability is the bacterial enzyme asparaginase, which digests asparagine. By analogy in breast and lung cancer, the metabolic vulnerability is the down-regulation of the thiamine transporter genes, the essential nutrient is thiamine, and the therapeutic agent to exploit the vulnerability is the bacterial enzyme thiaminase, which digests thiamine.

The enzyme thiaminase catabolizes thiamine and can cause acute thiamine deficiency Several forms of the enzyme thiaminase exist in nature, including plant, animal and bacterial forms of the enzyme. Since thiamine is an essential vitamin and since thiamine in excess is not known to be toxic, the physiologic role of thiaminase is not known.[5] The gene for the bacterial *Bacillus thiaminolyticus* thiaminase I gene has been cloned and characterized.[5] Although chronic thiamine starvation can result in severe neurologic symptoms and congestive heart failure (beriberi and Wernicke-Korsakoff syndromes), and would be an unacceptably toxic approach to cancer therapy, treatments that create acute, short-lived thiamine starvation would have less toxicity.

Furthermore, thiamine deprivation also affects chemotherapy sensitivity of cancer cells, and the cell culture models of thiamine starvation provide tools to evaluate the effect of thiamine starvation adaptation on sensitivity to chemotherapy and radiation. Thiamine starvation might affect chemotherapy for several reasons. Thiamine deprivation might augment the toxicity of drugs that are substrates for ATP-dependent drug efflux pumps (ABC transporters) because of less efficient ATP production. These drugs include doxorubicin and paclitaxel, both of which are pumped out of cells by the MDR1 drug efflux pump, and both of which are active drugs frequently used in breast cancer therapy. Mechanisms of resistance to alkylating agents utilize NADH and ATP to repair DNA damage, and require NADPH, a product of the transketolase-dependent (and thiamine dependent) pentose phosphate pathway, for the reduction and recycling of glutathione, a critical component of cellular detoxification pathways of alkylating agents.[8] Akt phosphorylation observed in the thiamine starvation adapted cells, has been linked in published studies to lung cancer resistance to etoposide[9,10,11], cyclophosphamide[10], cisplatinum[9], pactitaxel[9], and ionizing radiation[9,10]. Akt inhibition has also been linked to increase sensitivity to camptothecins[12], which are also used in lung cancer therapy.

The present studies demonstrate that thiamine starvation, both acute and long-term, is associated with changes in activation of genes, including Akt and HIF1, that regulate energy metabolism. While cancer cells are able to adapt to absolute thiamine starvation, the inability of HMEC to similarly adapt suggests that thiamine deprivation may reveal another difference in energy metabolism regulation between malignant and non-malignant cells that can be therapeutically exploited by creation of acute thiamine deficiency by administration of the thiaminase enzyme.

The present studies have also demonstrated phenotypic similarities between THTR2 down regulation and thiamine starvation that suggest that part of the cellular effect of THTR2 down regulation may be thiamine starvation, which may contribute to the characteristic alteration of energy metabolism in the cancer cell. Further understanding of the role of thiamine uptake and metabolism in cancer cells can provide an avenue for the therapeutic exploitation of the alteration of glucose metabolism in cancer.

Example 2

It was hypothesized that the down-regulation of thiamine uptake would make tumor cells more sensitive to thiamine starvation, a nutritional vulnerability that could be exploited clinically. Down-regulation of the thiamine transporter gene can be exploited by depleting the essential nutrient thiamine in breast cancer cells.

The idea that thiamine starvation, achieved through dietary restriction, would result in growth delay in a breast tumor xenograft was tested first. Next, the bacterial enzyme thiaminase I was tested as a therapeutic agent. The thiaminase was tested in breast cancer cell lines alone and in combination with doxorubicin and paclitaxel, chemotherapies that are frequently used in breast cancer treatment. By immunoblot analysis, the underlying cellular response of breast cancer cells to thiaminase I was explored.

Methods

Xenograft Experiments:

Studies were performed according to the University of Kentucky Institutional Animal Care and Use Committee guidelines. Female athymic nude mice (nu/nu) were obtained at 8-10 weeks of age. MDA231 cells grown were harvested in exponential growth phase, and resuspended in serum-free RPMI 1640. The mixture of 50 µl of cell suspension (5×10⁶ cells) and 50 µl of Matrigel™ Matrix (BD, Franklin Lakes, N.J.) were subcutaneously (SC) injected along one leg of animals. Following implantation the mice were placed in their cages and allowed to recover. Animals were fed either normal chow or the same chow without thiamine (TestDiet Richmond, Ind.) in cohorts of 3-4 mice per cohort. Tumor size was measured using calipers and tumor volumes were calculated using the following formula: tumor volume=$0.5 \times L \times W^2$, where L and W represent the largest diameter and the smallest diameter, respectively. Animal weights and tumor size (length and width) were measured every 2 days.

Thiaminase I Production:

The *E. coli* BL21 (DE3) thiaminase I overexpression stain was constructed by the Begley laboratory.[5] The expression vector pET22b(+) is IPTG-inducible and has an N-terminal polyhistidine tag that allows detection and efficient purification of the expressed recombinant enzyme. After IPTG-induction, cells were collected and lysed, and the recombinant enzyme was purified from cytosol using a HisTrap FF column (GE Healthcare, NJ) according to the manufacturer's protocol. Thiaminase I enzyme activity was determined with a spectrophotometric assay based on a method developed by Lienhard and modified by Costello and colleagues.[5] The assay is based on a change of absorbance at 252 nm resulting from the reaction of thiamine with secondary nucleophiles.

Cell Culture Conditions:

Human breast cancer cells MDA231, Hs578T, ZR75, MCF7 and T47D were obtained from the American Type Culture Collection (ATCC, Rockville Md.). Hs578T was maintained in DMEM, and the other cell lines were maintained in RPMI 1640, respectively. Both media were supplemented with 5% fetal calf serum and 1% penicillin/streptomycin in a humidified atmosphere of 5% $CO_2$.

Cytotoxicity Assays:

Breast cancer cells were plated in triplicate in 96-well microtiter plates in medium containing 5% fetal bovine serum at densities of 1000 cells/well. After 24 hours, medium containing thiaminase I was added to the cells. After 4-5 days, the cells were fixed in 10% trichloracetic acid, rinsed with water, and dried. The cells were stained with 0.4% sulforhodamine in 1% acetic acid, washed in 1% acetic acid, and dried as previously described.[13] The stained cells were solubilized in 200 ul of 10 mM Tris base pH 10.5, and the absorbance at 570 nm was determined on a microplate reader. The experiments were repeated 3 times in triplicate. The $IC_{50}$ was calculated from the dose response curve as the concentration of drug that produced a 50% decrease in the mean absorbance compared to the untreated wells using Prism GraphPad software. For synergy experiments, cells were plated at 3 concentrations of thiaminase I representing the approximate $IC_{40}$, $IC_{60}$ and $IC_{80}$ concentrations for each cell line, and then co-incubated in increasing concentrations of doxorubicin or paclitaxel. The experiments were repeated 3 times in triplicate and the results analyzed with Calcusyn software.

Determination of Cellular ATP Levels:

ATP was measured by a luciferin-luciferase assay using Bioluminescent Somatic Cell Assay kit (Sigma, Mo.). According to manufacturer's protocol, 100 µl of cell lysate was added to 100 µl of ATP assay mix solution and light emission was measured immediately with a luminometer (Monolight™ 3010, PharMingen). ATP concentrations were calculated from a calibration curve constructed for each experiment using standard ATP dissolved in the appropriate buffer in which the experiment was performed.

Immunoblot Analysis:

Cells were treated with thiaminase or anti-cancer agent for the indicated times and washed with ice-cold PBS. Cells were lysed with a triple-detergent lysis buffer (50 mM Tris pH8.0, 150 mM NaCl, 1% NP-40, 0.5% DOC, 0.1% SDS, 0.02% sodium azide and protease inhibitors). Equal amounts of protein were loaded into each well and separated by 10% SDS-PAGE gel, followed by transfer onto nitrocellulose membranes. The membranes were blocked, incubated with the indicated primary antibodies at 4° C. overnight, and the appropriate horseradish peroxidase-conjugated secondary antibody was added for 1 hour at room temperature. Immunoblots were developed by use of the enhanced chemiluminescence (ECL) detection system (Pierce, Rockford, Ill.) according to the manufacturer's protocol and autoradiography. All of the primary antibodies were purchased from Cell Signaling Technologies (Danvers, MA). The secondary antibodies were purchased from Sigma (St. Louis, Mo.). An anti-β-actin antibody was used as a control for protein loading.

Results

Figure 1B:
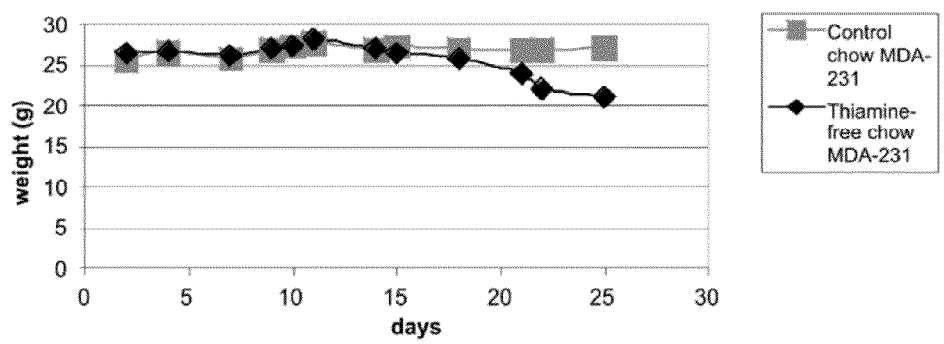
FIG. 1B is a graph showing the weight of the mice bearing the xenografts of FIG. 1A.

To determine whether thiamine starvation could cause tumor growth delay in a breast cancer xenograft, MDA231 cells were implanted subcutaneously in the flanks of nude mice and fed mice either a control diet or a diet in which thiamine was absent. As seen in FIG. 1A, the xenografts in the thiamine-starved mice showed tumor growth delay. Thiamine starvation was toxic over time, and animals began losing weight in the third week, as illustrated by FIG. 1B. Although thiamine starvation through a dietary approach would not be tolerable, this study demonstrated the potential for a therapeutic response of breast cancer cells to acute thiamine deprivation by administration of the thiaminase I enzyme.

Figure 2:
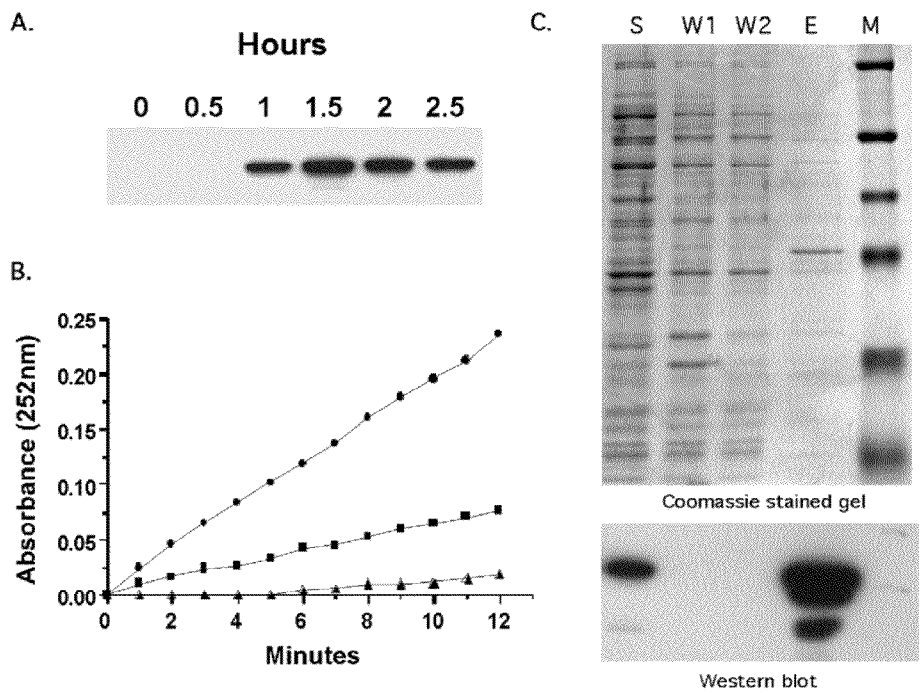
FIG. 2A is an immunoblot showing detection of an expressed recombinant thiaminase.
FIG. 2B is a graph showing the results of a spectrophotometic assay confirming activity of the expressed recombinant thiaminase.
FIG. 2C includes a Coomassie stained gel, including a purified protein of the expected size (about 48 kDa) in lane E and a Western Blot, identifying the thiaminase using an anti-polyhistidine tag antibody.

To explore acute thiamine starvation of breast cancer cells through a pharmacologic approach, a recombinant thiaminase I enzyme from *Bacillus thiaminolyticus* was produced. FIG. 2A demonstrates detection of recombinant thiaminase I in crude bacterial lysate with the antibody against the polyhistidine tag linker. Recombinant thiaminase I expression in BL21(DE3) cells following induction with 2 mM IPTG was achieved. Immunoblots were performed against the polyhistidine tag linker using the monoclonal Anti-Xpress™ antibody (Invitrogen). The activity of the recombinant enzyme was confirmed by a spectrophotometric assay. With reference to FIG. 2B, thiaminase 1 activity was determined spectrophotometrically at 252 nm; samples include: buffer alone (▲); 20 µl of bacterial lysate prior to IPTG induction (0 hrs) (●); and 20 µl of bacterial lysate 1.5 hrs after IPTG induction (●).

Thiaminase I was purified using a nickel-charged sepharose resin column (HisTrapFF). As shown in FIG. 2C, Western blot and Coomassie stained gels of thiaminase I-expressing BL21(DE3) bacteria induced with IPTG were obtained. The top gel is a Coomassie stained gel showing size fractionated proteins from the purification steps. The bottom gel is a Western blot of a replicate gel probed with a monoclonal antibody against the polyhistidine tag. S, bacterial supernatant before applying to column; W1 and W2, column washes; E, eluate of the column with the fraction containing the recombinant thiaminase I protein; M, marker (the 4th marker band from the top is 47.5 kDa). As shown, one of the elution fractions from the purification column, marked lane E, contains a purified protein that is of the expected size (47.5 kDa), which is identified by the anti-polyhistidine tag antibody.

The cytotoxicity of various concentrations of thiaminase I in breast cancer cell lines was studied. Cell lines included in the study were MCF-7, T47D, ZR-75, HS578T, MDA231/

Figure 3:
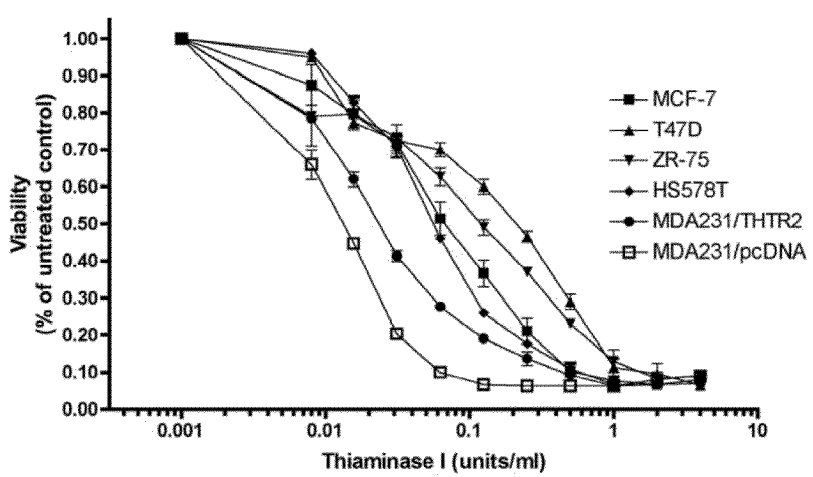
FIG. 3 is a graph showing the results of a cytotoxicity assay of breast cancer cell lines exposed to increasing concentrations of thiaminase.

THTR2, which are MDA231 cells transfected with the THTR2 thiamine transporter, and MDA231/pcDNA, which are MDA231 cells transfected with the empty expression vector. As shown in FIG. 3, thiaminase I $IC_{50}$ s were spread over an 18-fold range, from 0.012 U/ml to 0.22 U/ml. Of interest, the MDA231 cell line transfected with the thiamine transporter THTR2 (MDA231/THTR2) showed a 67% increase in resistance compared to empty vector control MDA231 cells (0.020±0.003 U/ml vs 0.012±0.001 U/ml). $IC_{50}$ values for the other cell lines were MCF-7 0.06±0.012 U/ml; T47D 0.22±0.09 U/ml; ZR-75 0.12±0.04 U/ml; and HS578T 0.05±0.005 U/ml.

Figure 4A:
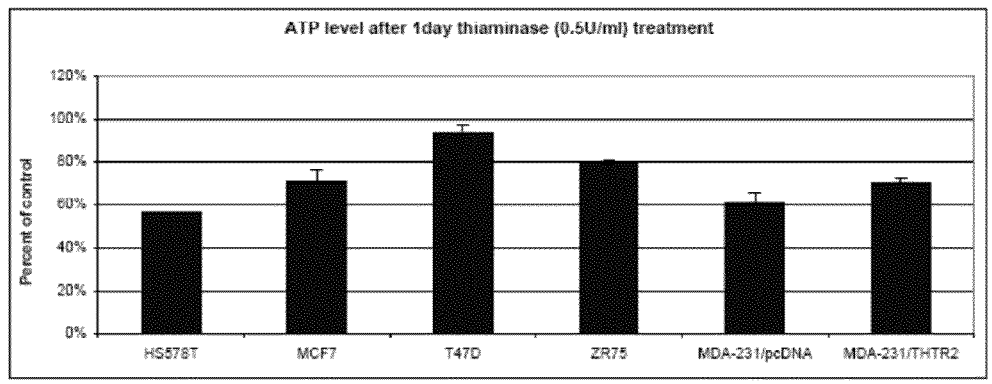
FIG. 4A is a graph showing ATP levels in cell lines treated with 0.5 U/ml thiaminase 1 for 1 day.
Figure 4B:
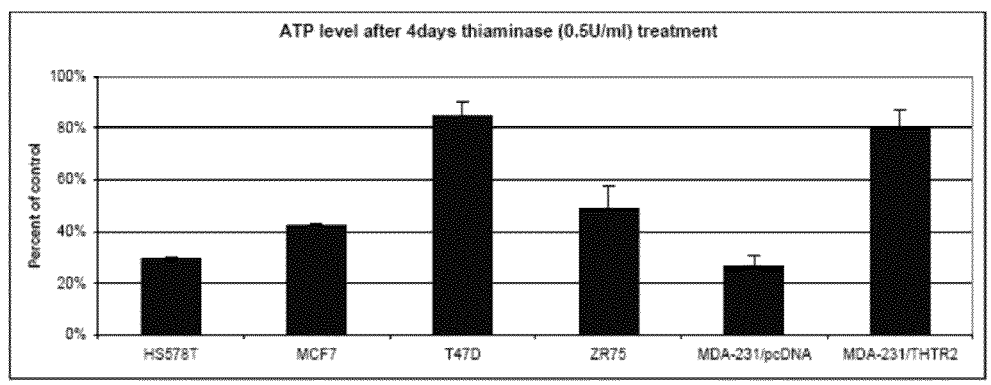
FIG. 4B is a graph showing ATP levels in cell lines treated with 0.5 U/ml thiaminase 1 for 4 days.
Figure 4C:
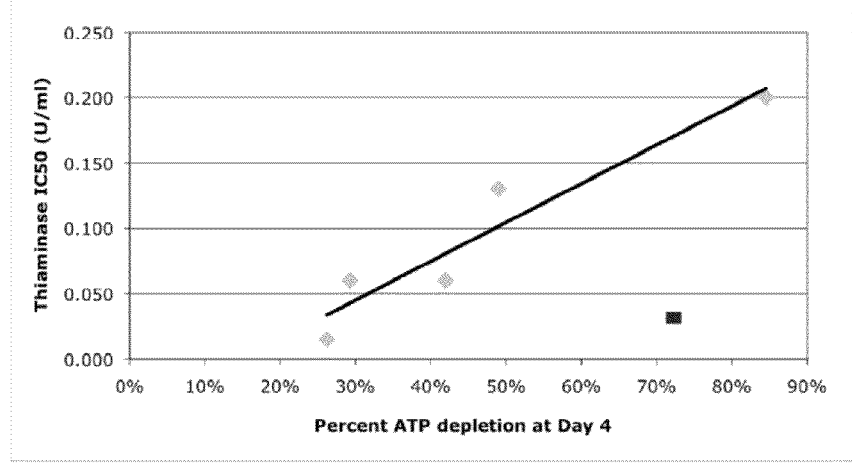
FIG. 4C is a graph showing ATP depletion after 4 days as a function of thiaminase $IC_{50}$.
Figure 5A:
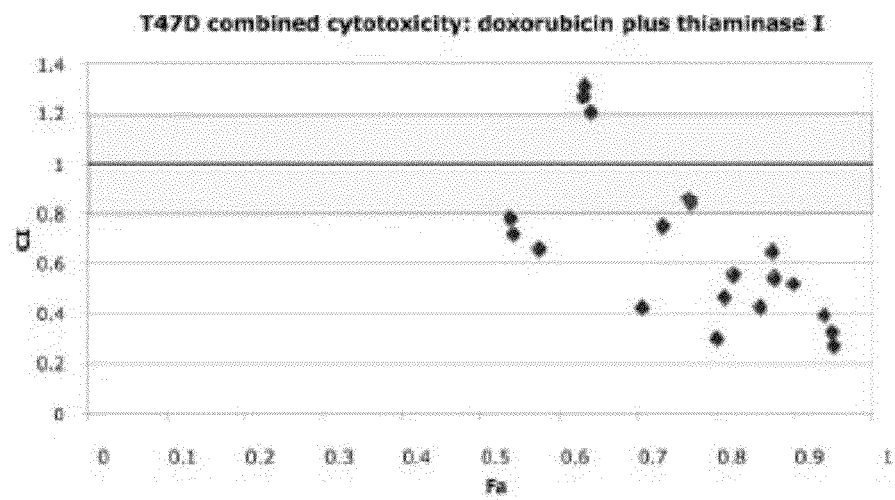
FIG. 5A is a graph showing combination index (CI) as a function of combined cytotoxicity (Fa) of thiaminase and doxorubicin in T47D breast cancer cells.
Figure 5B:
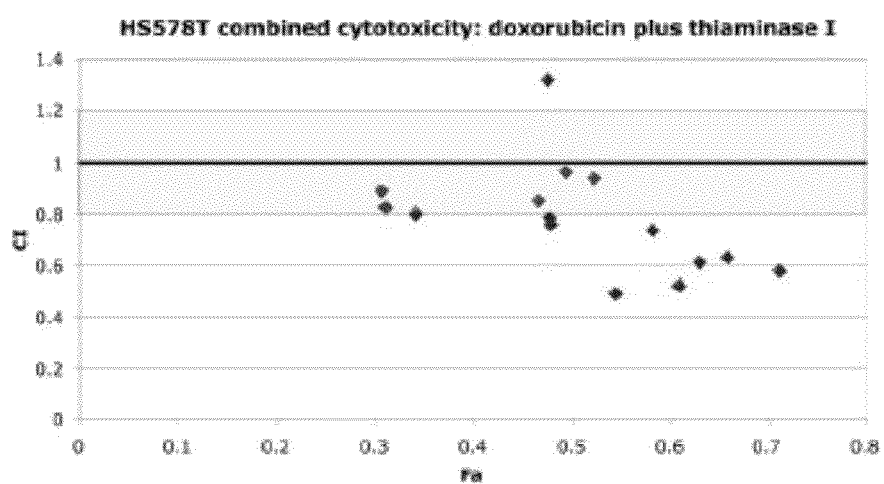
FIG. 5B is a graph showing combination index (CI) as a function of combined cytotoxicity (Fa) of thiaminase and doxorubicin in HS578T breast cancer cells.
Figure 5C:
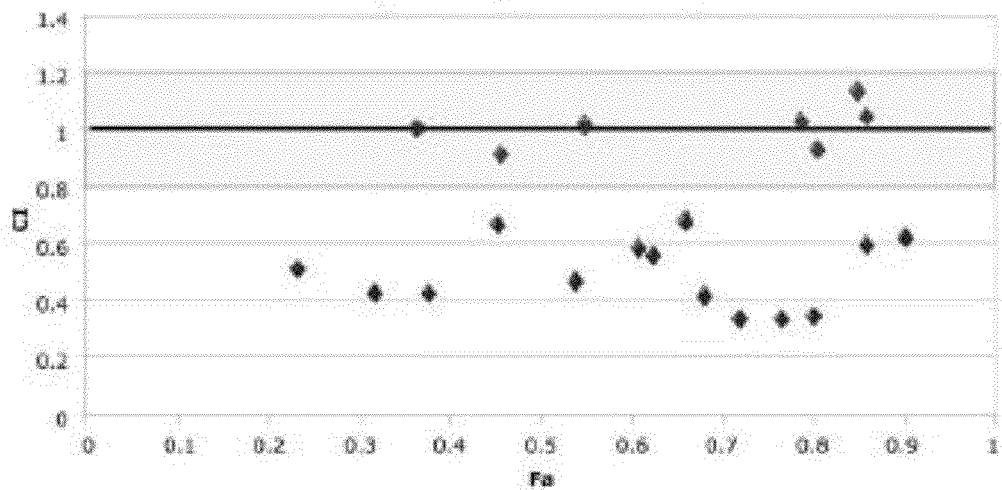
FIG. 5C is a graph showing combination index (CI) as a function of combined cytotoxicity (Fa) of thiaminase and doxorubicin in ZR75 breast cancer cells.
Figure 5D:
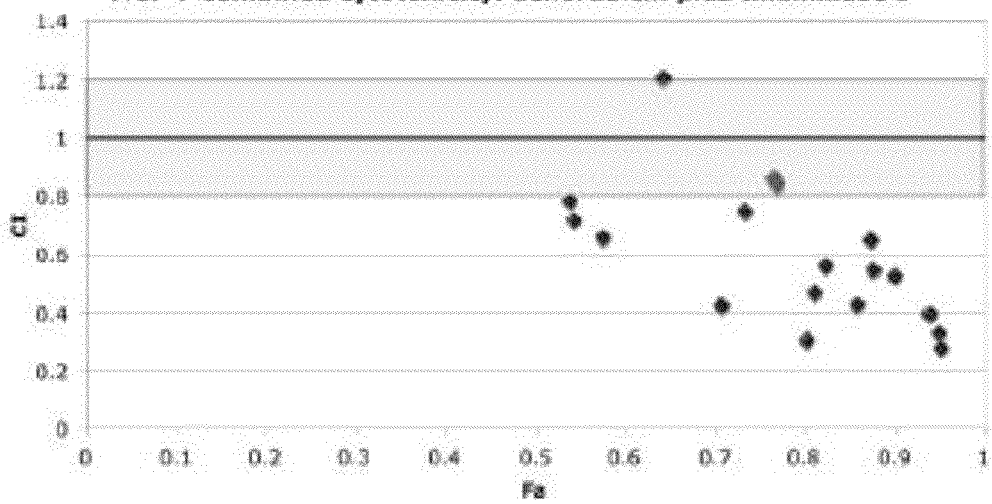
FIG. 5D is a graph showing combination index (CI) as a function of combined cytotoxicity (Fa) of thiaminase and doxorubicin in MCF-7 breast cancer cells.
Figure 5E:
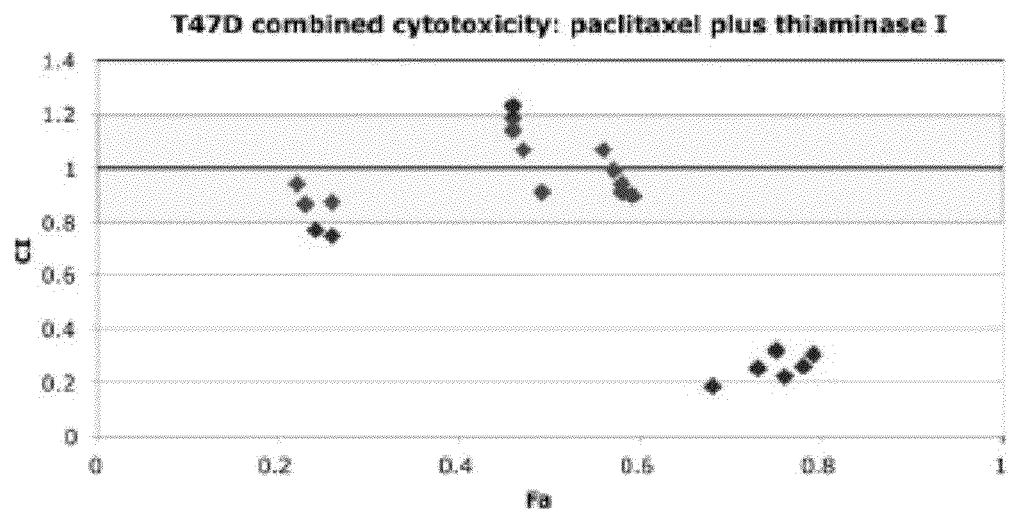
FIG. 5E is a graph showing combination index (CI) as a function of combined cytotoxicity (Fa) of thiaminase and paclitaxel in T47D breast cancer cells.
Figure 5F:
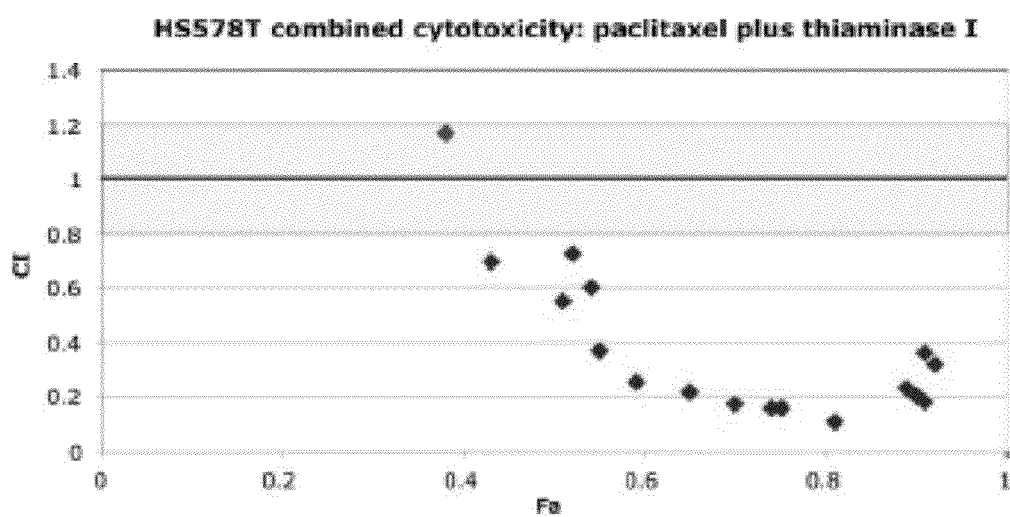
FIG. 5F is a graph showing combination index (CI) as a function of combined cytotoxicity (Fa) of thiaminase and paclitaxel in HS578T breast cancer cells.
Figure 5G:
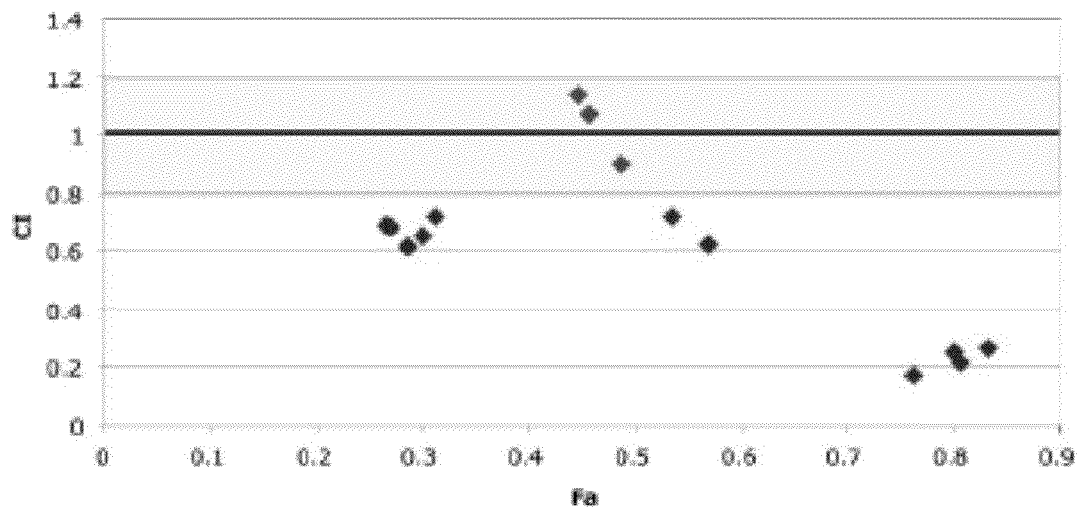
FIG. 5G is a graph showing combination index (CI) as a function of combined cytotoxicity (Fa) of thiaminase and paclitaxel in ZR75 breast cancer cells.
Figure 5H:
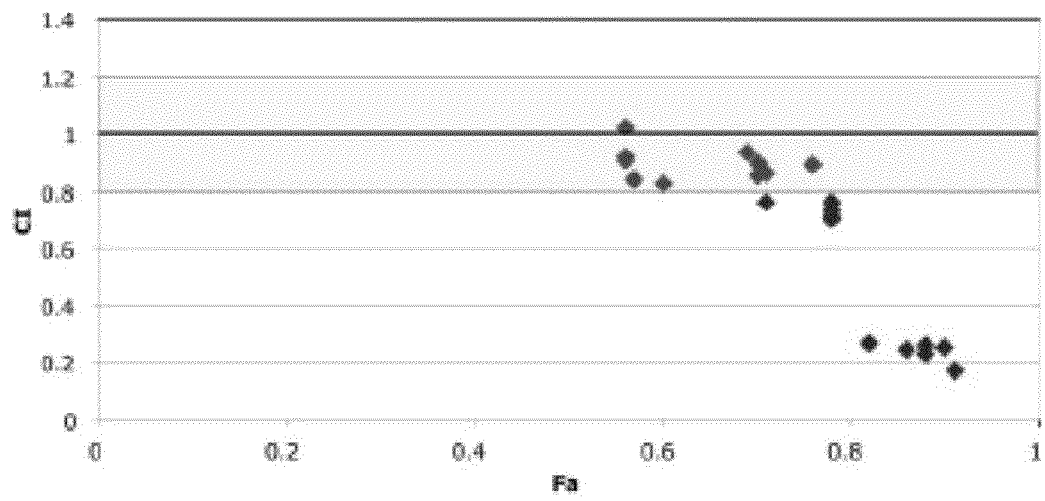
FIG. 5H is a graph showing combination index (CI) as a function of combined cytotoxicity (Fa) of thiaminase and paclitaxel in MCF-7 breast cancer cells.

Since thiamine depletion affects ATP production, studies were conducted to determine whether thiaminase I treatment decreased cellular ATP levels. As shown in FIGS. 4A and 4B, ATP depletion after incubation in 0.5 U/ml thiaminase I after 1 day (FIG. 4A) and after 4 days (FIG. 4B) was variable in different cell lines. After 4 days, the ATP depletion effect was most pronounced in MDA231/pcDNA cells (26% of control) and Hs578T cells (29% of control), and least pronounced in T47D cells (84% of control). The correlation between the $IC_{50}$ s in FIG. 3 and ATP depletion after 4 days in FIG. 4B is shown in FIG. 4C. With the exception of the MDA231 cells transfected with THTR2 (square), there is a strong linear relation between thiaminase I-mediated ATP depletion and thiaminase I cytotoxicity ($r^2=0.91$).

To determine whether thiaminase I treatment would have additive or synergistic activity with two anti-cancer agents commonly used in breast cancer treatment, doxorubicin and paclitaxel cytotoxicity in breast cancer cell lines were examined during co-incubation with thiaminase I. Dose response curves were analyzed using the median-dose effect model (Calcusyn), and multiple combination indices (CI's) were calculated over a range of concentrations for each anti-cancer agent/thiaminase combination. The cells were incubated for 4-5 days in increasing concentrations of the anti-cancer agent/thiaminase combinations and surviving cells were determined as described above. The Combination Index (CI) was calculated for each combination of thiaminase I and anti-cancer agent using Calcusyn software, and the CIs plotted against the combined cytotoxicity (Fa) to demonstrate additivity or synergy over a range of combinations and cytotoxic effects.

As seen in FIGS. 5A-5H, the CI was less than 0.8 for most drug-thiaminase I combinations in the four breast cancer cell lines for both doxorubicin and paclitaxel, indicating a synergistic interaction, and the remaining CI's were in the 0.8-1.2 range, indicating additive cytotoxicity. These data suggest that acute thiamine starvation may improve the effectiveness of breast cancer chemotherapy.

Figure 6:
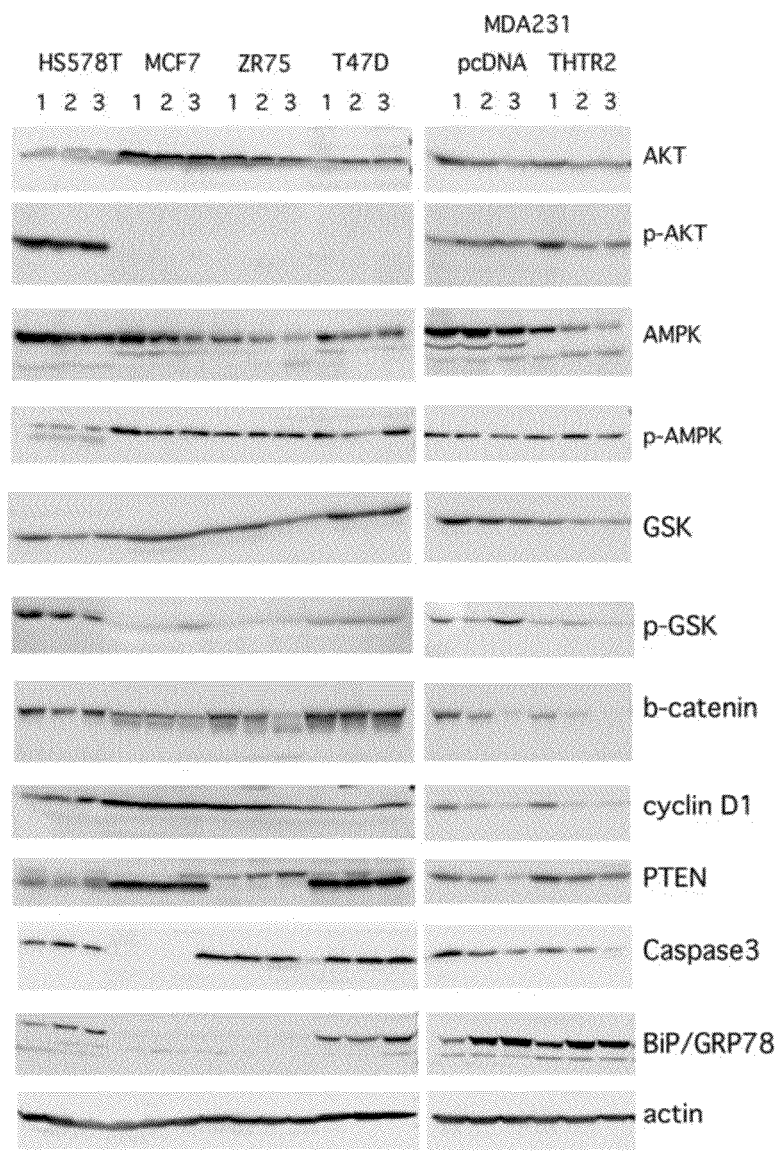
FIG. 6 includes the results of immunoblot analyses of Akt, p-Akt, AMPK, p-AMPK, GSK3β, p-GSK3β, β-catenin, cyclin D1, PTEN, caspase 3 and GRP78 in breast cancer cells after exposure to thiaminase.

Since thiaminase I decreases ATP levels in breast cancer cells and could be expected to alter cellular energy regulation, energy pathways in breast cancer cells after thiaminase I treatment were examined. Immunoblot analyses of Akt, p-Akt, AMPK, p-AMPK, GSK3β, p-GSK3β,β-catenin, cyclin D1, PTEN, caspase 3, and GRP78 was conducted in HS578T, MCF7, ZR75, and T47D breast cancer cell lines plus MDA231 breast cancer cells transfected with THTR2 or empty vector pcDNA as a control after exposure to thiaminase I. Cytosolic protein (30 µg) was probed using standard immunoblot procedures with antibodies as described in Methods. With reference to FIG. 6, there was no consistent change in Akt, AMPK, or GSK-3b expression or phosphorylation among the breast cancer cell lines under the conditions studied. The only consistent change observed was an increase in GRP78 expression, suggesting activation of the unfolded protein response (UPR).

To further examine the effect of thiaminase I on the UPR, HS578T, MCF7, ZR75, and T47D breast cancer cell lines were exposed to tunicamycin (5 µg/ml) and thapsigargin (1 µM), which were used as positive controls for stimulating the UPR, as well as to thiaminase I. The cells were then analyzed for UPR activation by immunoblot analysis of UPR pathway proteins GRP78, CHOP, p-PERK, and p-EIF2α.

Figure 7:
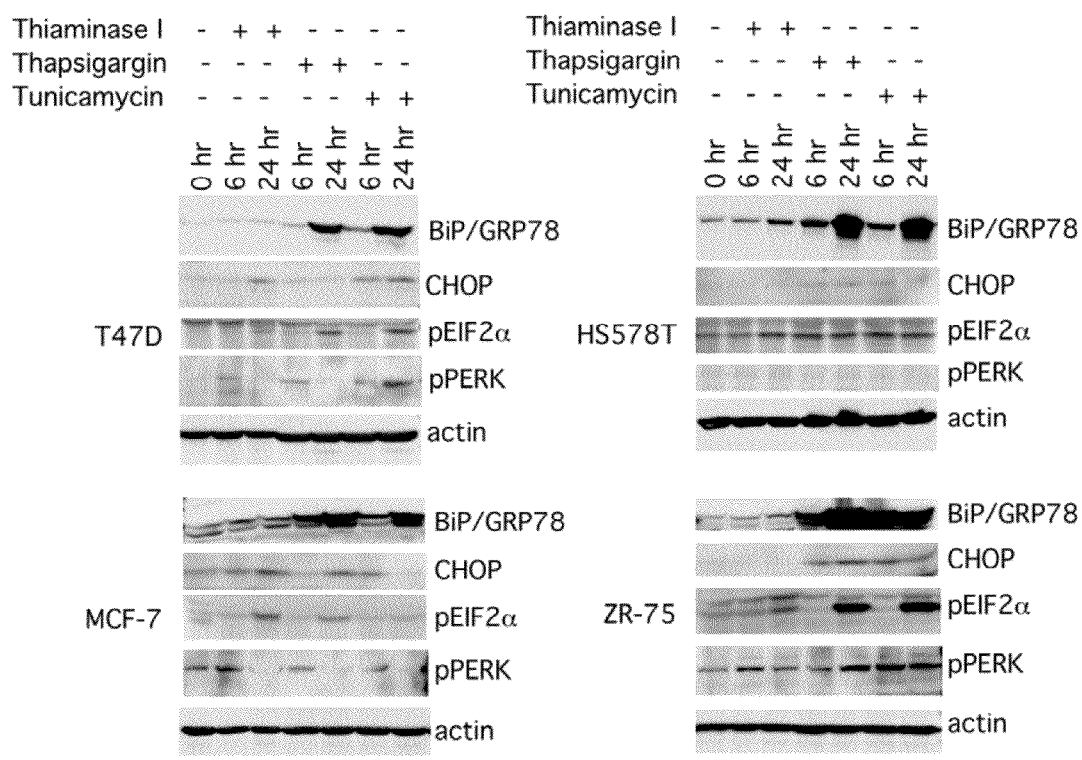
FIG. 7 includes the results of immunoblot analyses of UPR pathway proteins GRP78, CHOP, p-PERK, and p-EIF2α after exposure to thiaminase in MCF-7, ZR-75, T47D and HS578T breast cancer cell lines.

With reference to FIG. 7, all four breast cancer cell lines showed a marked induction in GRP78 after thapsigargin and tunicamycin exposure, with variable activation of downstream effectors CHOP, p-EIF2a, and p-PERK. The three breast cancer cell lines most sensitive to thiaminase I, ZR-75, MCF-7 and HS578T, all showed induction of GRP78. MCF-7 and ZR-75 cells also showed downstream activation of p-PERK and p-EIF2a after thiaminase I exposure.

Discussion

Chronic thiamine starvation is toxic, leading to the neurological and cardiovascular symptoms of beriberi and Wernicke-Korsakov syndrome, and could not realistically be considered as an anticancer therapeutic approach. However, acute short-lived thiamine starvation could have less toxicity, and could be achieved by administration of a thiaminase. Thiaminase catabolizes thiamine and can cause acute thiamine deficiency. Several forms of the enzyme thiaminase exist in nature, including plant, animal, and bacterial forms of the enzyme.[14-16] Since thiamine is an essential vitamin and since thiamine in excess is not known to be toxic, the physiologic role of thiaminase is not known.[5]

Although the down-regulation of thiamine transporter gene THTR2 expression may represent a nutritional vulnerability, it was not clear whether thiamine was relevant to tumor growth. FIG. 1 illustrates that an MDA231 breast cancer xenograft shows growth delay in mice fed a thiamine-free diet, even though this nutritional deprivation had expected toxicities after a 3 week period.

Previous studies of thiamine starvation have utilized thiamine analogs, such as pyrithiamine and oxythiamine and amprolium, which all compete for uptake and may inhibit thiamine dependent enzymes.[6,7] Bettendorff and colleagues have previously reported that adaptation to physiologic (6 nM) extracellular thiamine concentration still required addition of the thiamine analog amprolium to observe a decrease ATP levels in cultured neuroblastoma cells.[6] However, uncertainty about the extent of both thiamine uptake inhibition and extent of thiamine-dependent enzyme inhibition by thiamine analogs led Applicants to conclude that these analogs could not definitively mimic acute thiamine starvation.

Instead of thiamine antagonists the potential therapeutic efficacy a thiaminase was explored. As noted above, the bacterial enzyme thiaminase I was selected for studies described herein. As shown in FIG. 3, thiaminase I was toxic to all breast cancer cell lines tested, indicating that acute thiamine deprivation has toxic consequences in breast cell lines. In addition, there was a 1.8-fold difference in the cytotoxic $IC_{50}$ between MDA231 cells transfected with the transporter, vs control MDA231 cells. In previous studies the cellular effects of altered THTR2 expression by transfecting cancer cells with THTR2 were explored.[4] RNA microarray studies identified genes that were up- and down-regulated with increased THTR2 expression. In comparing tumor cells to non-malignant tissues, the pattern of gene expression predicted by the microarray experiments was reflected in subsequent studies of RNA levels in tumors compared to non-malignant adjacent tissue, and in THTR2 knock-down experiments.[4] The studies here indicate that the down regulation of THTR2 observed in breast cancer cells may increase their sensitivity to acute thiamine starvation.

The possibility that thiamine deprivation might also enhance chemotherapy sensitivity in breast cancer cells was also studied. Thiamine starvation could sensitize cancer cells to chemotherapy for several reasons. Thiamine deprivation might augment the toxicity of drugs that are substrates for ATP-dependent drug efflux pumps (ABC transporters) because of less efficient ATP production. These drugs include doxorubicin and paclitaxel, both of which are pumped out of cells by the MDR1 drug efflux pump, and both of which are active drugs frequently used in breast cancer therapy. As shown in FIG. 5, at almost all concentration combinations, thiaminase I was additive or synergistic with paclitaxel and doxorubicin in all four breast cancer cell lines in which these synergy studies were performed.

Surprisingly, given the decrease in ATP levels in all breast cancer cell lines after thiaminase I exposure, there was no consistent increase in proteins involved in energy sensing and regulation, including phosphorylation of Akt, AMPK or GSK3b after thiaminase I treatment (FIG. 6). However, GRP78 protein expression was also examined because of the possibility that inhibition of thiamine-dependent pathways might result in protein damage that could create endoplasmic reticulum stress and trigger the unfolded protein response (UPR). The sensing chaperone GRP78 sequesters three proteins in the endoplasmic reticulum (PERK, IRE1 and ATF6) resulting in UPR activation.[17,18]

All of the breast cancer cell lines showed significant increase in GRP78 in response to thapsigargin and tunicamycin (FIG. 7). There was variation, however, in downstream effects among the four breast cancer cell. Similarly thiaminase I, while not as potent a GRP78 inducer as thapsigargin or tunicamycin, also showed variable response downstream of GRP78. UPR can activate both pro-survival and pro-apoptotic pathways, and the variability in downstream activation among breast cancer cell lines is apparent in FIG. 7, making the effect of UPR activation on cell survival difficult to predict. GRP78 overexpression confers anticancer drug resistance against several classes of agents in cell lines from varied tumors of origin[19] while knocked down expression of GRP78 increased sensitivity to cells to anticancer drugs.[20] Thus, it is not clear whether UPR activation by thiaminase I directly results in apoptosis activation, or contributes to the observed synergy with chemotherapeutic agents, in breast cancer cells. Nevertheless, such synergy was found.

Example 3

Thiaminase I, obtained as described above in Example 2, was submitted to the NCI60 Drug Screening program for screening in 60 cancer cell lines. The results from the NCI60 program reveal that the methods of treating cancer as described herein are effective against various types of cancer.

Figure 8:
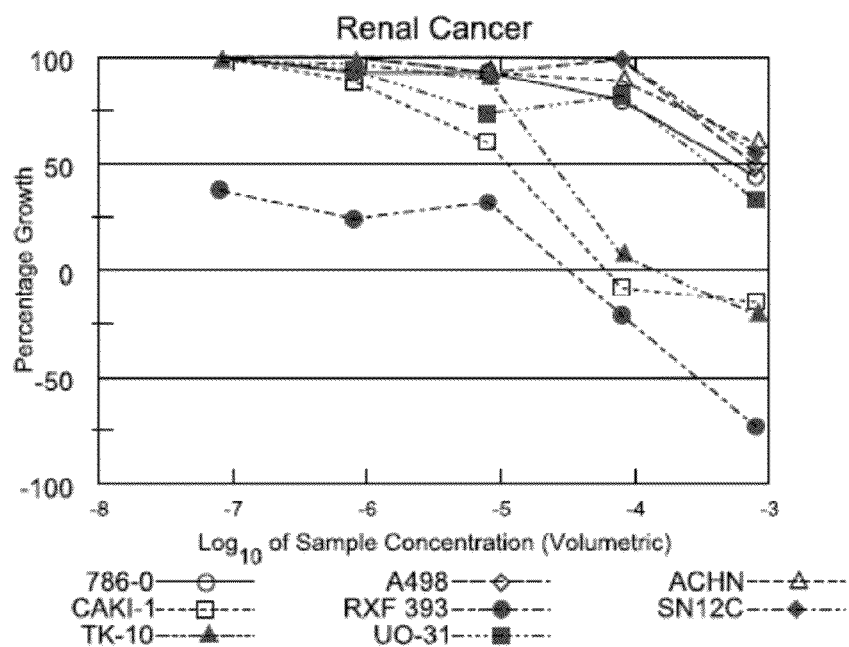
FIG. 8 is a graph showing dose response of renal cancer cells to thiaminase for 786-0, A498, ACHN, Caki-1, RXF 393, SN12C, TK-10, and UO-31 renal cancer cell lines.

The cytotoxicity of various concentrations of thiaminase I in renal cancer cell lines was studied. Cell lines included in the study were 786-0, A498, ACHN, Caki-1, RXF 393, SN12C, TK-10, and UO-31. As shown in FIG. 8, the renal cancer cell lines were sensitive to thiaminase I. The sensitivity of the renal cancer cells to thiaminase I indicates that the methods of treating cancer as described herein have utility in renal cancer.

Figure 9:
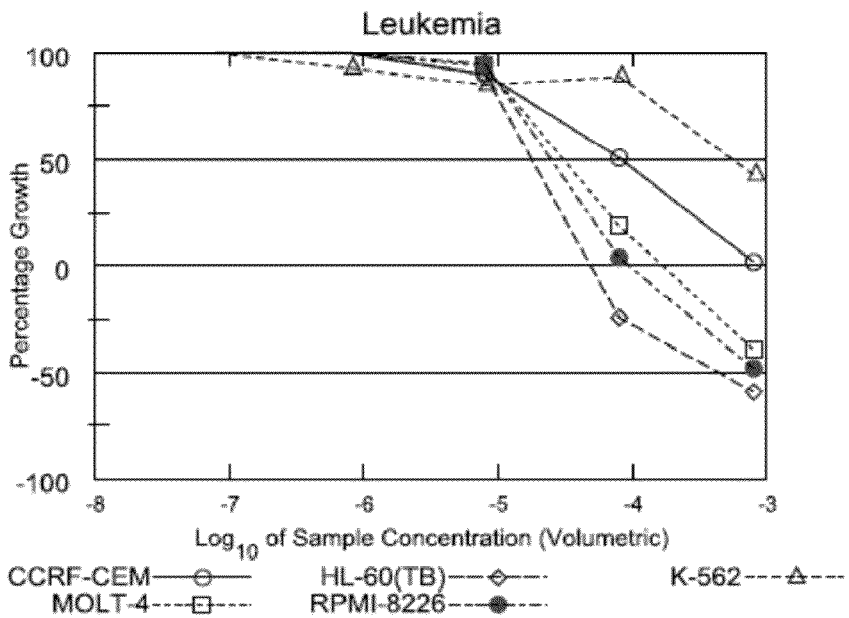
FIG. 9 is a graph showing dose response of leukemia cells to thiaminase for CCRF-CEM, HL60(TB), K-562, MOLT-4, and RPMI-8226 leukemia cell lines.

The cytotoxicity of various concentrations of thiaminase I in leukemia cell lines was studied. Cell lines included in the study were CCRF-CEM, HL60(TB), K-562, MOLT-4, and RPMI-8226. As shown in FIG. 9, the leukemia cell lines were sensitive to thiaminase I. The sensitivity of the leukemia cells to thiaminase I indicates that the methods of treating cancer as described herein have utility in leukemia.

Figure 10:
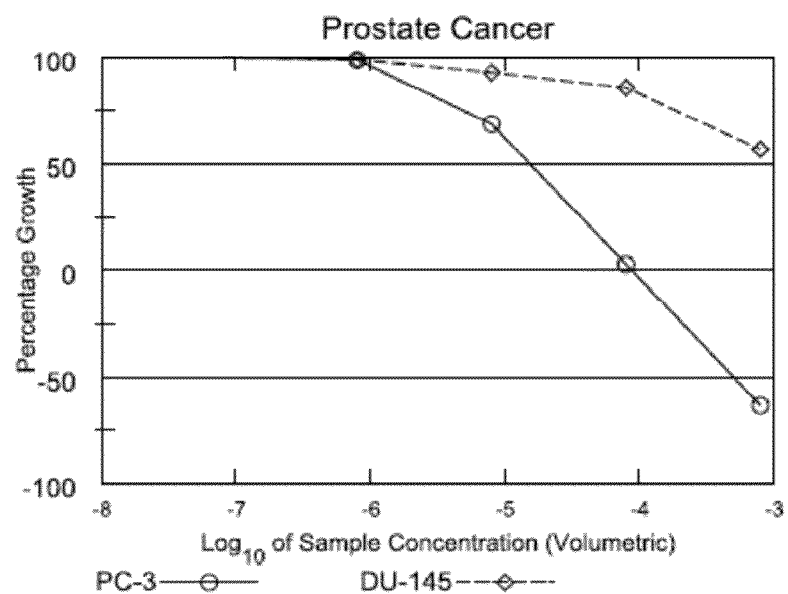
FIG. 10 is a graph showing dose response of prostate cancer cells to thiaminase for PC-3 and DU-145 prostate cancer cell lines.

The cytotoxicity of various concentrations of thiaminase I in prostate cancer cell lines was studied. Cell lines included in the study were PC-3 and DU-145. As shown in FIG. 10, the prostate cancer cell lines were sensitive to thiaminase I. The sensitivity of the prostate cancer cells to thiaminase I indicates that the methods of treating cancer as described herein have utility in prostate cancer.

Figure 11:
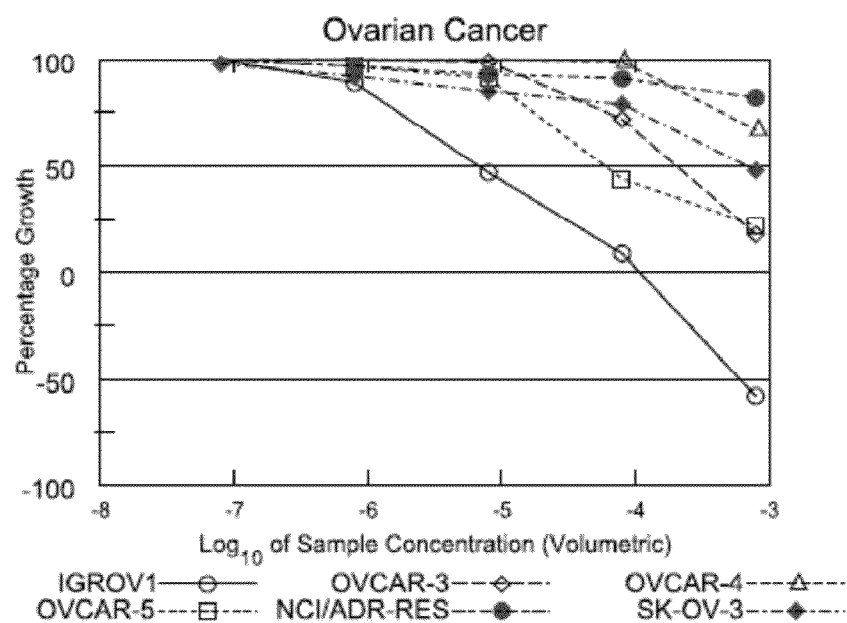
FIG. 11 is a graph showing dose response of ovarian cancer cells to thiaminase for IGROV1, OVCAR-3, OVCAR-4, OVCAR-5, NCI/ADR-RES, and SK-OV-3 ovarian cancer cell lines.

The cytotoxicity of various concentrations of thiaminase I in ovarian cancer cell lines was studied. Cell lines included in the study were IGROV1, OVCAR-3, OVCAR-4, OVCAR-5, NCI/ADR-RES, and SK-OV-3. As shown in FIG. 11, the ovarian cancer cell lines were sensitive to thiaminase I. The sensitivity of the ovarian cancer cells to thiaminase I indicates that the methods of treating cancer as described herein have utility in ovarian cancer.

Figure 12:
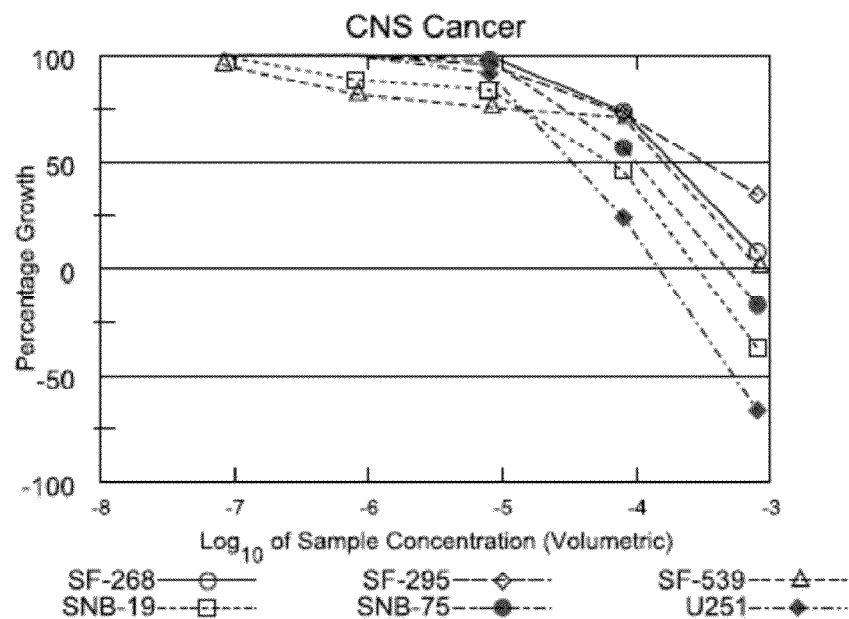
FIG. 12 is a graph showing dose response of central nervous system (CNS) cancer cells to thiaminase for SF-268, SF-295, SF-539, SNB-19, SNB-75, and U251 CNS cancer cell lines.

The cytotoxicity of various concentrations of thiaminase I in central nervous system (CNS) cancer cell lines was studied. Cell lines included in the study were SF-268, SF-295, SF-539, SNB-19, SNB-75, and U251. As shown in FIG. 12, the CNS cancer cell lines were sensitive to thiaminase I. The sensitivity of the CNS cancer cells to thiaminase I indicates that the methods of treating cancer as described herein have utility in CNS cancer.

Figure 13:
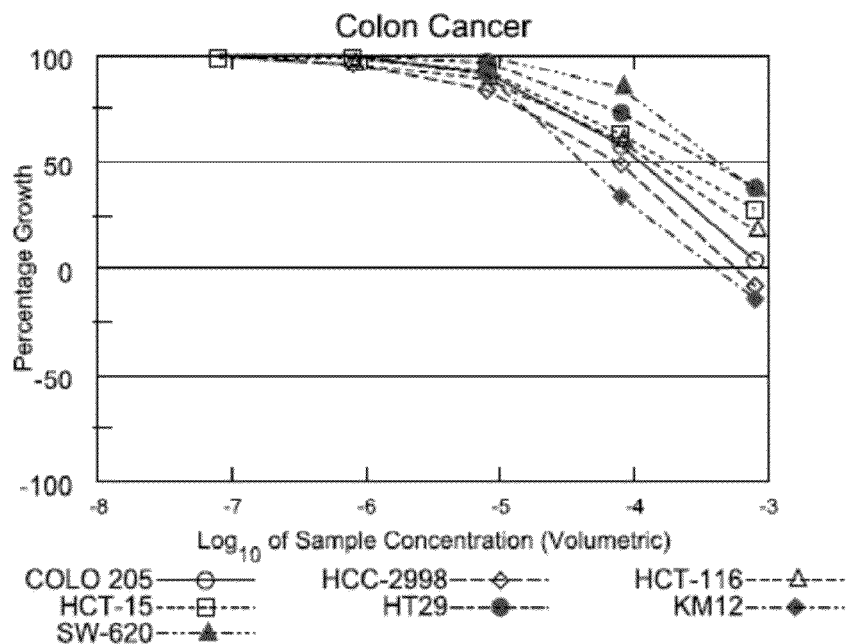
FIG. 13 is a graph showing dose response of colon cancer cells to thiaminase for COLO205, HCC-2998, HCT-116, HCT-15, HT29, KM12, and SW-620 colon cancer cell lines.

The cytotoxicity of various concentrations of thiaminase I in colon cancer cell lines was studied. Cell lines included in the study were COLO205, HCC-2998, HCT-116, HCT-15, HT29, KM12, and SW-620. As shown in FIG. 13, the colon cancer cell lines were sensitive to thiaminase I. The sensitivity of the colon cancer cells to thiaminase I indicates that the methods of treating cancer as described herein have utility in colon cancer.

Figure 14:
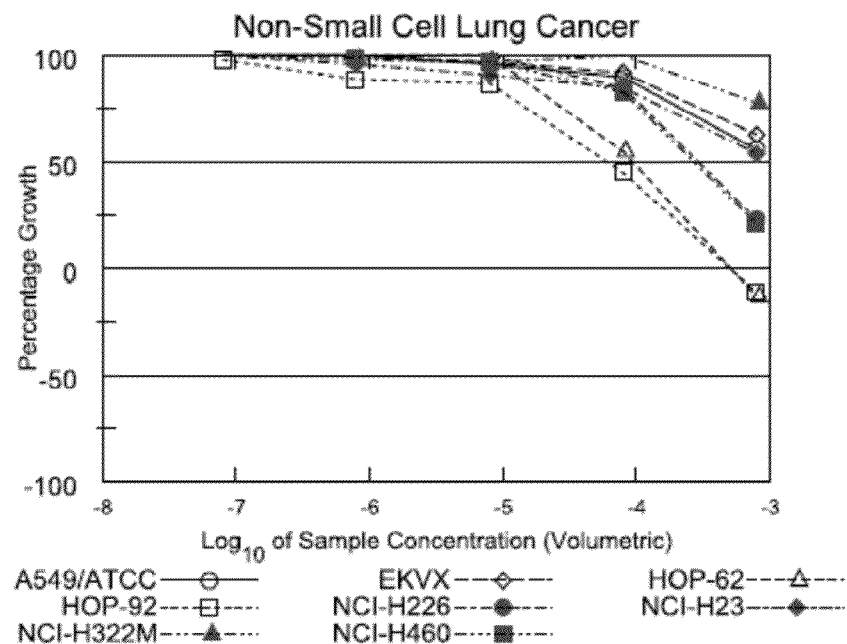
FIG. 14 is a graph showing dose response of non-small cell lung cancer cells to thiaminase for A549/ATCC, EKYX, HOP-62, HOP-92, NCI-H226, NCI-H23, NCI-H322M, and NCI-H460 non-small lung cancer cell lines.

The cytotoxicity of various concentrations of thiaminase I in non-small cell lung cancer cell lines was studied. Cell lines included in the study were A549/ATCC, EKYX, HOP-62, HOP-92, NCI-H226, NCI-H23, NCI-H322M, and NCI-H460. As shown in FIG. 14, the non-small cell lung cancer cell lines were sensitive to thiaminase I. The sensitivity of the non-small cell lung cancer cells to thiaminase I indicates that the methods of treating cancer as described herein have utility in non-small cell lung cancer.

Figure 15:
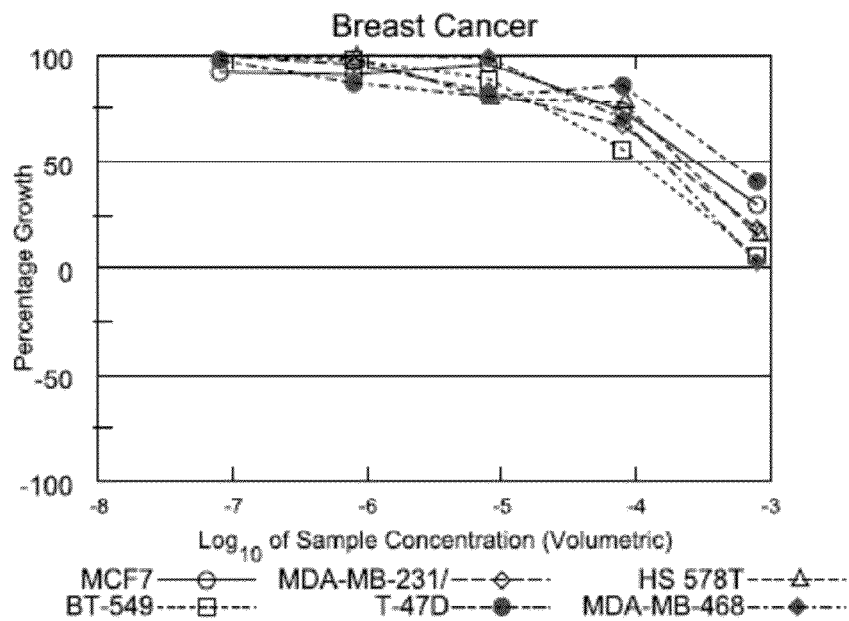
FIG. 15 is a graph showing dose response of breast cancer cells to thiaminase for MCF-7, MDA-MB-231, HS 578T, 8T-549, T-47D, and MDA-MB-468 breast cancer cell lines.

The cytotoxicity of various concentrations of thiaminase I in breast cancer cell lines was studied. Cell lines included in the study were MCF-7, MDA-MB-231, HS 578T, 8T-549, T-47D, and MDA-MB-468. As shown in FIG. 15, the breast cancer cell lines were sensitive to thiaminase I. The sensitivity of the breast cancer cells to thiaminase I indicates that the methods of treating cancer as described herein have utility in breast cancer.

Figure 16:
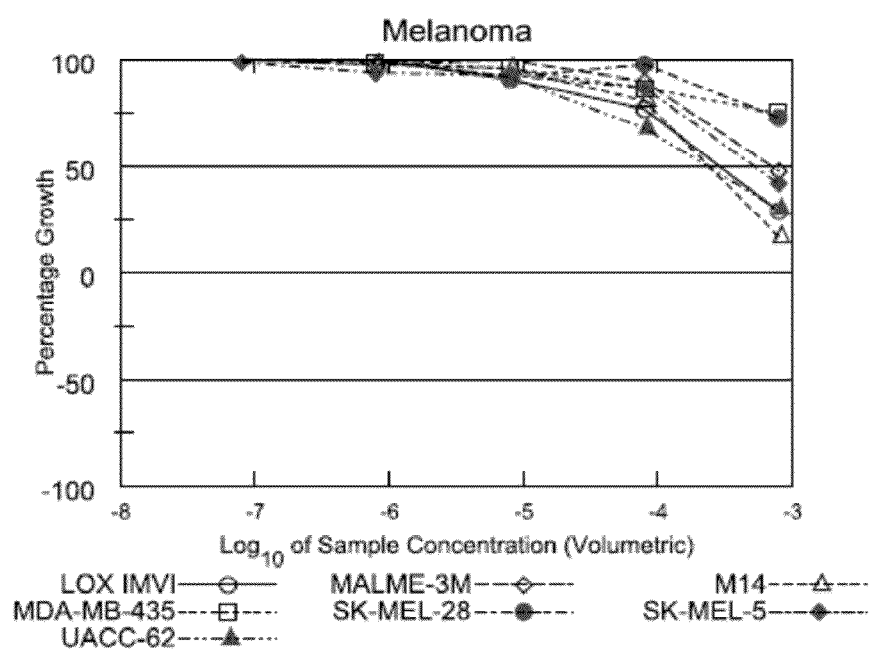
FIG. 16 is a graph showing dose response of melanoma cells to thiaminase for LOX IMVI, MALME-3M, M14, MDA-MB-435, SK-MEL-28, SK-MEL-5, and UACC-62 melanoma cell lines.

The cytotoxicity of various concentrations of thiaminase I in melanoma cell lines was studied. Cell lines included in the study were LOX IMVI, MALME-3M, M14, MDA-MB-435, SK-MEL-28, SK-MEL-5, and UACC-62. As shown in FIG. 16, the study indicates that there is activity against the melanoma cell. The activity of the thiaminase I against the melanoma cells indicates that the methods of treating cancer as described herein have utility in melanoma.

The following is prophetic. Studies are conducted to determine the cytotoxic activity of thiaminase I in combination with anti-cancer agents in renal cancer cells, leukemia cells, prostate cancer cells, ovarian cancer cells, central nervous system (CNS) cancer cells, colon cancer cells, non-small cell lung cancer cells, and melanoma cells in vitro; and in in vivo models of renal cancer, leukemia, prostate cancer, ovarian cancer, central nervous system (CNS) cancer, colon cancer, non-small cell lung cancer, and melanoma.

Studies to determine the cytotoxic activity of thiaminase I in cancer are conducted as follows. Studies are conducted using renal cancer cells, leukemia cells, prostate cancer cells, ovarian cancer cells, central nervous system (CNS) cancer cells, colon cancer cells, non-small cell lung cancer cells, and melanoma cells in vitro, treated with thiaminase alone and in combination with anti-cancer agents currently used to treat such cancers. A panel of cell lines are studied in in vitro cytotoxicity assays in a 96-well microtiter plate format using a sulforhodamine dye assay. For synergy experiments, the cancer cell lines are incubated in thiaminase I, representing $IC_{40}$-$IC_{90}$ concentrations for each cell line, and serial concentrations of anti-cancer agents active in such cancers (e.g., docetaxel, paclitaxel, and estramustine) are added.

The combination index for each thiaminase I/anti-cancer agent combination is calculated using Calcusyn software to determine additivity, synergy, or antagonism of thiaminase/ anti-cancer agent combinations. It is found that the cancer cells are sensitive to the thiaminase/anti-cancer agent combinations, and additivity and/or synergy is observed. Studies conducted in in vivo cancer models also show that the cancers are sensitive to thiaminase/anti-cancer agent combinations, and additivity and/or synergy is observed.

Acute thiamine starvation may cause a lethal insult to cancer cells by mechanisms that are not identified at this time. FIGS. 8-16 demonstrate broad anticancer activity of thiaminase I in cell lines from multiple different tumor types. In addition, in different cell lines from the same malignancy, such as prostate cancer, there is a wide variation in sensitivity of tumor cells to thiaminase I. These observations suggest that certain types of cancer cells may have markers of sensitivity to thiaminase I. Since it is known that tumor cells have an alteration of energy metabolism called the Warburg effect, it is possible that there are different mechanisms underlying the Warburg effect and that some may confer sensitivity to acute thiamine withdrawal.

Example 4

With reference to FIG. 10, the cytotoxicity of various concentrations of thiaminase I in prostate cancer cell lines was studied. Cell lines included in the study were PC-3 and DU-145. As shown in FIG. 10, the prostate cancer cell lines were sensitive to thiaminase I. The sensitivity of the prostate cancer cells to thiaminase I indicates that the methods of treating cancer as described herein have utility in prostate cancer. The marked sensitivity of PC-3 cells to thiaminase I prompted the design of additional studies to examine use of thiaminase in a method of treating prostate cancer. The following is prophetic.

Studies are conducted to determine the cytotoxic activity of thiaminase I in prostate cancer cell lines in vitro in combination with anti-cancer agents currently used to treat prostate cancer; and in in vivo models of prostate cancer. A formulation of thiaminase is developed to optimize efficacy. The mechanism of cytotoxicity of thiaminase I in prostate cancer cells is studied.

Studies to determine the cytotoxic activity of thiaminase I in prostate cancer are conducted as follows. Studies are conducted using prostate cancer cell lines in vitro, alone and in combination with anti-cancer agents currently used to treat prostate cancer: A panel of prostate cancer cell lines (PC-3, DU-145 and LNCaP) are studied in in vitro cytotoxicity assays in a 96-well microtiter plate format using a sulforhodamine dye assay. For synergy experiments, the prostate cancer cell lines are incubated in thiaminase I, representing $IC_{40}$-$IC_{90}$ concentrations for each cell line, and serial concentrations of anti-cancer agents active in relapsed prostate cancer (e.g., docetaxel, paclitaxel, and estramustine) are added.

The combination index for each thiaminase I/anti-cancer agent combination is calculated using Calcusyn software to determine additivity, synergy, or antagonism of thiaminase/ anti-cancer agent combinations. It is found that prostate cancer cells are sensitive to the thiaminase/anti-cancer agent combinations, and additivity and/or synergy is observed. Studies conducted in in vivo prostate cancer models also show that the prostate cancer is sensitive to thiaminase/anti-cancer agent combinations, and additivity and/or synergy is observed.

Studies are conducted using xenograft models of prostate cancer: The maximum tolerated dose (MTD) of thiaminase I in nude mice feeding on standard chow when administered as a daily IP injection has been established. The cell lines are grown as subcutaneous xenografts and tumor growth inhibition to thiaminase I administration is determined. Tumor growth is found to be inhibited by thiaminase I administration.

A formulation of thiaminase is developed to optimize efficacy. It is contemplated that the pharmacologic properties of recombinant thiaminase I can be improved by increasing plasma retention time by developing a formulation of thiaminase. The thiaminase is decorated through PEGylation with various molecular weight (2, 5 and 12 kDa) polymers; thiaminase nanoparticles formation is incorporated from functional poly(ethylene glycol)-poly(amino acid) block copolymers; and enzyme activity of formulated thiaminase is determined using a spectrophotometric assay. Cytotoxicity of formulated and intact thiaminase are compared in prostate cancer cell lines. Prostate cancer cells are found to be sensitive to formulated thiaminase.

The mechanism of cytotoxicity of thiaminase I in prostate cancer cells is studied. Thiamine starvation has the potential to alter energy regulation of cells, and breast cancer cell lines exposed to thiaminase I increase expression of GRP78 (as noted in the Example above). Proteins are proved, including Akt and pAkt, AMPK and p-AMPK, ACC and p-ACC, GSK3β and p-GSK3β, and NF-κB, all of which are involved in regulation of either glucose metabolism, in alternative pathways of energy production, or in regulation of cell survival. Also ER stress response are examined by probing GRP78 levels. Other proteins are examined based upon initial results.

Example 5

A PEGylated thiaminase was prepared. Thiaminase I was modified at its N-terminus with PEG having a MW of 5K. PEGylation was also conducted by modifying C-terminus of thiaminase I with 12K PEG as a comparison. Briefly, NHS-activated PEG (5K) was mixed with thiaminase I at an excess (10-fold) amount in HEPES reaction buffer for 3 h. PEGylated thiaminase I (PEG-thiaminase) was purified by ultrafiltration. C-terminus PEGylation was carried out using coupling reagents (1-Ethyl-3-[3-dimethylaminopropyl] carbodiimide hydrochloride and N-hydroxysulfosuccinimide). Concentrations and activity of PEG-thiaminase were determined subsequently. Preliminary data demonstrate that the N-terminus PEGylation retains biological activity of thiaminase I. The thiaminase I PEGylated at C-terminus with the 12k PEG did not retain biological activity.

Example 6

The following example is prophetic, notwithstanding the numerical values, results and/or data referred to and contained in the example.

Mouse Xenograft Models for Thiaminase Treatment

Glucose metabolism is aberrantly regulated in cancer cells. This abnormal utilization of glucose in cancer cells (called the Warburg effect) is the underlying principle behind new PET scan technology that has improved lung cancer detection. The vitamin thiamine is a co-factor for several enzymes in glucose metabolic pathways. In vitro experiments demonstrate that cancer cells adapted to thiamine starvation are more sensitive to radiation than control cells, suggesting that alterations in cancer cell energy metabolism created by thiamine deprivation can be exploited clinically. Therefore, there is a need to determine how acute thiamine starvation enhances radiation therapy in a xenograft model, i.e. inducing tumors in nude mice.

Acute thiamine starvation can be created clinically by administration of the bacterial enzyme thiaminase I. If thiamine starvation and/or recombinant thiaminase I treatment can enhance the radiation responsiveness of lung and breast cancer xenografts, then a rationale is established for the advancement of thiaminase I as a potential therapeutic agent. In these studies, the period of thiamine starvation in mice lasts two weeks, and then all mice are returned to a normal diet to prevent symptoms of chronic thiamine deficiency.

Methods

Female athymic nude mice (nu/nu) ranging in age between 8-12 weeks (18-22 g) are used. Animals are received and housed for one week in microisolator or PIV cages prior to the following procedures.

Week 1—The ability of a nude mice strain to tolerate 2 weeks of thiamine starvation is determined. In this step, mice are fed thiamine-free chow or thiamine-free chow with the thiamine antagonists oxythiamine or pyrithiamine for 2 weeks and observed for toxicity, including weight loss and neurologic symptoms. After two weeks normal mouse chow is fed to the mice. The mice in this step are divided into 5 groups with one group fed normal chow, one group fed normal chow and receiving intraperitoneal (IP) injections of sterile saline one time each day, one group fed thiamine-free chow, one group fed thiamine free chow and receiving IP injections of oxythiamine at 200 mg/kg one time each day, and one group fed thiamine free chow and receiving IP injections of pyrithiamine at 0.5 mg/kg one time each day.

The oxythiamine and pyrithiamine are prepared in sterile saline. The abdominal skin of each mouse is cleansed with 70% alcohol and oxythiamine or pyrithiamine is administered by intraperitoneal (IP) injection, in a volume of approximately 200 µl, using a 27G needle to minimize discomfort. IP injection is done at 10:00 am every day, and the site of the injection is rotated to minimize discomfort.

Week 3—The maximum tolerated dose (MTD) of thiaminase I administration is determined in mice fed a normal diet and in mice fed a thiamine free diet. In this step, the mice are divided into five groups with one group fed normal chow and receiving IP injections of saline one time each day, one group fed normal chow and receiving IP injections of thiaminase at 0.01 units per kg one time each day, one group fed normal chow and receiving IP injections of thiaminase at 0.1 units per kg one time each day, one group fed normal chow and receiving IP injections of thiaminase at 1 unit per kg one time each day, and one group fed normal chow and receiving IP injections of thiaminase at 10 units per kg one time each day. The mice will be observed for toxicity and after two weeks the mice are fed a normal diet. IP injections are done as described above with the thiaminase being administered in a 200 µl volume.

Week 5—The third step is to determine the viability of tumor xenografts in thiamine-deprived mice. Human lung cancer cells H460 and human breast cancer cells MDA-MB-231 grown in vitro, are harvested in exponential growth phase and resuspended in in vitro culture medium (DMEM+5% FCS) supplemented with penicillin-streptomycin solution (50 units of penicillin and 50 µg of streptomycin/ml) at $5 \times 10^7$ cells/ml. 100 µl of cell suspension ($5 \times 10^6$ cells) are subcutaneously (SC) injected into the flank of the mice using a 25 Gauge needle. Following implantation the mice are placed in their cage and allowed to recover. Tumors are implanted no earlier than day 8 after arrival and the experiment is initiated when tumor diameters are approximately 6-8 mm. Depending on the tumor line, the growth of the tumors to approximately 6-8 mm in diameter may take 1-2 weeks. Tumor volume (TV) is calculated with the following formula: $TV=[(?/6) \times L \times W^2]$, where L is length, and W is width. Animals with tumors greater than 1500 mm$^3$ are euthanized. Once the tumors become palpable (6-8 mm), the mice are divided into groups with one group fed normal chow, one group fed thiamine-free chow, one group fed thiamine-free chow and receiving IP injections of oxythiamine at 200 mg/kg one time each day, one group fed thiamine free chow and receiving IP injections of pyrithiamine at 0.5 mg/kg one time each day, and one group fed thiamine-free chow and receiving thiaminase at an MTD dose one time each day.

The experimental period lasts two weeks after these treatments, and then all mice are returned to a normal diet to prevent symptoms of chronic thiamine deficiency. The mice are weighed twice per week and animals exhibiting a weight loss of >20% are euthanized to avoid animal suffering. 6 mice are used for each treatment using each cell line. There are two cell lines, so 60 mice are used. 2 repetitions per experiment are needed for statistical significance, so a total of 120 mice are used for this step. Again, IP injections are done as described above.

Week 16—The fourth step is to irradiate the tumors in thiamine-deprived mice. Xenografts are established as described above and when the growing tumor volume reaches 300-400 mm$^3$ in size, the tumor and a 1 cm margin is treated with gamma-rays through an open field at 5 Gy/fraction for a total dose of 25 Gy. Radiation dose may be modified depending on the response of the control tumors. Mice receiving radiation are briefly sedated using isoflurane.

Tumor bearing mice have their tumors treated in a conformal manner (focused radiation, using a collimated beam of radiation, thus reducing the volume of the mouse being exposed to radiation therapy) using x-irradiation. The tumor and a 1 cm margin is irradiated, thus, the remainder of the animal receives no primary radiation exposure and very limited scatter exposure.

The experimental period lasts two weeks, and then all mice are returned to a normal diet to prevent symptoms of chronic thiamine deficiency. The mice are weighed every two days and animals exhibiting a weight loss of >20% are euthanized to avoid animal suffering. 6 mice are used for each treatment as in the third step. There are 5 treatments, 2 different cancer cell lines, 2 total radiation doses, and 2 repetitions per experiment, so a total of 240 mice are used in this step. After finishing every experiment, the mice are euthanatized using overdose carbon dioxide ($CO_2$) followed by thoracotomy. A reduction in tumor size is observed in the thiamine-deprived mice that receive a combination of thiaminase and radiation, indicating that a method including administering thiaminase in combination with radiation is useful for treating cancer.

As an alternative fourth step, the thiamine-deprived mice are treated with thiaminase in combination with an anti-cancer agent. Xenografts are again established as described above and when the growing tumor volume reaches 300-400 mm³ in size, the tumor bearing mice are treated with thiaminase in combination with doxorubicin. In this alternative fourth step, the mice are divided into five groups with one group fed normal chow and receiving IP injections of saline one time each day, one group fed normal chow and receiving IP injections of thiaminase at 0.01 units per kg one time each day, one group fed normal chow and receiving IP injections of thiaminase at 0.1 units per kg one time each day, one group fed normal chow and receiving IP injections of thiaminase at 1 unit per kg one time each day, and one group fed normal chow and receiving IP injections of thiaminase at 10 units per kg one time each day. All groups receive doxorubicin at doses of 20 mg/kg, but the doxorubicin dose can be modified depending on the response of the control tumors.

The alternative experimental period lasts two weeks, and then all mice are returned to a normal diet to prevent symptoms of chronic thiamine deficiency. The mice are weighed every two days and animals exhibiting a weight loss of >20% are euthanized to avoid animal suffering. 6 mice are used for each treatment and since there are 5 treatments, 2 different cancer cell lines, and 2 repetitions per experiment, a total of 120 mice are used in this alternative step. After finishing every experiment, the mice are euthanized using overdose carbon dioxide ($CO_2$) followed by thoracotomy. A reduction in tumor size is observed in the thiamine-deprived mice that receive thiaminase in combination with doxorubicin, indicating that a method including administering thiaminase in combination with an anti-cancer agent is useful for treating cancer.

Example 7

The present inventors had shown that the bacterial enzyme thiaminase I has anti-tumor activity. In an attempt to make thiaminase I a more effective pharmaceutical agent, it was modified it by adding various length polyethylene glycol (PEG) chains.

The present inventors surprisingly discovered that a 5k-PEGylation eliminated thiaminase cytotoxic activity in all cell lines tested. Both native thiaminase and 5k-PEGylated thiaminase efficiently depleted thiamine from cell culture medium. Both native and 5k-PEGylated thiaminase could utilize intracellular phosphorylated thiamine as substrates; however, native enzyme more effectively depleted thiamine and thiamine diphosphate in RS4 leukemia cell cytosol. Despite the lack of in vitro cytotoxicity, PEGylation markedly increased the in vivo toxicity of the enzyme. The dose limiting toxicity of PEGylated thiaminase appeared to be GI toxicity, not heart and brain toxicity as would be expected to result from thiamine starvation. Pharmacokinetic studies revealed that the half-life of native thiaminase was 1.5 hours compared with 34.4 hours for the 5k-PEGylated enzyme. Serum thiamine levels were depleted by both native and 5k-PEGylated enzyme. Despite superior pharmacokinetics, 5k-PEGylated thiaminase showed no anti-tumor effect against an RS4 leukemia xenograft, in contrast to native thiaminase which showed anti-tumor activity. To summarize, it was found that PEGylation of thiaminase I enhances plasma retention time but diminishes its in vitro cytotoxicity profile, increases its in vivo toxicity, and decreases its activity against a leukemia xenograft, the opposite of the desired effects. These studies suggest that the mechanism of anticancer cytotoxicity of thiaminase depends on intracellular thiamine catabolism, while systemic toxicity is related to extracellular thiamine depletion.

Introduction. Thiamine is a vitamin cofactor in enzyme complexes that play key roles in central carbon metabolism (Vander Heiden, et al., 2009). Extracellular thiamine is transported into the cell by two specific transporters, and is phosphorylated into its biologically active forms. Thiamine pyrophosphate (TPP), the diphosphate form, is the cofactor form of thiamine and is required for pyruvate dehydrogenase complex, which facilitates the catalysis of glucose-derived pyruvate and formation of acetyl CoA. The latter enters the tricarboxylic acid cycle for the efficient extraction of energy from its chemical structure. In addition TPP is a cofactor for transketolase, another key step in a different pathway that extracts the carbon from glucose for production of biomass. Other intracellular forms of phosphorylated thiamine include thiamine monophosphate, thiamine triphosphate and adenosine thiamine triphosphate (Gangolf, et al., 2010). Bettendorff and colleagues have recently shown wide variation in intracellular concentrations of thiamine and phosphorylated thiamine pools in various tissues. (Gangolf, et al., 2010).

The dysregulation of central carbon metabolism in cancer has been the target of many different anticancer strategies (Vander Heiden, et al., 2009). The present inventors have focused at disruption of thiamine metabolism in cancer, a strategy that was derived from initial observations that tumors down-regulate thiamine uptake transporters (Liu, et al., 2003; Liu, et al., 2004). The present inventors have found that recombinant thiaminase enzyme is cytotoxic in breast cancer cells (Liu, et al., 2010) and that a chemically modified 1k-PEGylated form of thiaminase has growth inhibitory effects at very low concentrations in leukemia cell lines (Daily, et al., 2011).

These observations led to attempts to optimize thiaminase enzyme with a series of modifications in the hope of improving its 'drugability'. The present inventors studied linear chain, polyethylene glycol modified 1k-5k- and 10k-forms of thiaminase, with most of the focus on 5k-PEGylated with respect to cytotoxic potency, pharmacokinetics and pharmacodynamics. The present inventors intended to arrive at a formulation that would have superior tolerability and efficacy that could be taken forward as a lead agent for further preclinical development. Also, by studying different modifications, the present inventors hoped to gain a better understanding of the mechanism of action of the drug. As expected, PEGylation improved that plasma retention time, with the 5k-PEGylated form appearing to be superior to 1k- and 10k-PEG modifications. Surprisingly, however, PEGylation with the longer chains abrogated in vitro cytotoxic activity of thiaminase, was less tolerable, and eliminated thiaminase activity against an RS4 leukemia xenograft model. In short, 5k-PEG modification of thiaminase had the exact opposite of the desired effect, but did result in insight into the mechanism of anti-tumor action of thiaminase enzyme.

Methods

Enzyme production: Native recombinant thiaminase I was purified from bacterial culture using the *E. coli* BL21 (DE3) thiaminase I overexpressing strain provided to us by the Begley laboratory (Costello, et al., 1996) and purified as previously described (Liu, et al., 2010).

Enzyme activity assays: Two methods were used to determine enzyme activity. One assay, using aniline as a nucleophile, was used to measure enzyme activity of purified products (Costello, et al., 1996). The present inventors found that this method was not suitable for pharmacokinetic studies, as hemoglobin in serum interfered with detection. Therefore, a different method, using 2-nitrothiolphenol as a nucleophile, was used for enzyme detection in pharmacokinetic studies (Hanes, et al., 2007). For determination of substrate utilization, thiamine monophosphate and thiamine diphosphate were substituted for thiamine at the same concentrations.

PEGylation: Linear chain methoxy-poly(ethylene glycol) (PEG: 1 kDa, Thermo Scientific; and 5 kDa and 10 kDa, NanoCS) was used for PEGylation of thiminase I. All PEG chains were activated with N-Hydroxysuccinimide (NHS) esters in order to modify primary amino groups on the enzyme. NHS-activated PEG reagents were dissolved in anhydrous dimethyl sulfoxide (DMSO) at 250 mM while thiaminase I was dissolved in 10 mM HEPES buffer at 10 mg/ml. PEGylation reactions were initiated by mixing these solutions at room temperature. The reactions were allowed to proceed for 3 h, followed by repetitive ultrafiltration using 10 kDa molecular weight cut-off membranes to remove DMSO. Concentrated PEGylated enzymes were purified by fast protein liquid chromatography (FPLC: Bio-Rad Biologic equipped with Superose 12 10/300 GL column, PBS 1×). 20Linear chain PEGylated thiaminase enzyme (LCPTE) with high purity was isolated by fraction collection. Buffer solutions were subsequently replaced with deionized water. Purified LCPTE was sterilized by 0.22 µm membrane filtration and freeze-dried for storage at −20° C.

LCPTE Physical Characterization: Dynamic light scattering (DLS) measurements were conducted to determine hydrodynamic diameters of native and PEGylated enzymes by using a particle size detector (Zetasizer Nano-ZS, Malvern). Samples (2 mg/ml) were placed in disposable cuvettes and measurements were conducted with 173° backscattering settings. Particle size was measured in triplicate.

Cytotoxicity assays: Human breast cancer cell lines MCF7 and MDA-231, human prostate cancer cell line PC-3, human lung cancer cell line H460, human glioma cell line LN18, and leukemia cell line Molt-4 were obtained from ATCC; human ovarian cancer cell line IGROV1 were obtained from NCI; leukemia cell lines Reh, RS4 and Jurkat were generously provided by Dr. Terzah Horton, Baylor College of Medicine. Cell line authentication was performed after all studies had been completed by PCR amplification of 9 short tandem repeat (STR) loci (Research Animal Diagnostic Laboratory, St. Louis), and comparing the profile to the ATCC STR database. All cell lines were confirmed to be of human origin. The STR profile of MCF-7, MDA-231, PC-3, H460, LN-18, Reh and Jurkat cell lines were identical to the ATCC profile. The Reh cell line matched all alleles in the ATCC Reh profile plus one extra allele at 2 loci. Cells were plated in triplicate in 96-well microtiter plates in RPMI-1640 (with 25 mM HEPES) medium containing 10% fetal bovine serum at final densities between 3 to $8 \times 10^4$ cells/well (optimal conditions for each cell line were determined by assay). Medium containing native thiaminase or 5k-PEGylated thiaminase at a concentration range of $1 \times 10^{-6}$ to 4 units/ml was added to cells and incubated for 4 days. Following incubation, an MTT Cell Proliferation Assay (ATCC) was performed according to the ATCC protocol (optimal conditions were initially determined for each cell line). The $IC_{50}$ was calculated from the dose response curve as the concentration of drug producing a 50% decrease in the mean absorbance compared to the untreated wells using Prism GraphPad software. The cytotoxicity experiments were repeated a minimum of three times in triplicate.

Thiamine assay: For quantitative determination of thiamine, the present inventors implemented a previously published HPLC/fluorescence assay for indirect detection of thiamine, by derivatizing thiamine to thiochrome using potassium ferricyanide, with slight modifications (Lu, et al., 2008). An Agilent C18, 5 µm particle size 4.6×250-mm column was used for reversed phase chromatography. An isocratic elution was used for medium and serum, and the mobile phase consisted of dibasic sodium phosphate (25 mmol/L, pH7.0) and methanol, 50:50, vol/vol (1 ml/min). The injection volume was 5 µl. Thiochrome was detected at an excitation wavelength of 375 nm and emission wavelength of 435 nm. Quantitative relationships were determined based on peak area. The limit of quantitation was 0.3 nM. For determination of intracellular thiamine catabolism, RS4 cells were incubated with native thiaminase and 5k-PEGylated thiaminase at a concentration of 1 unit/ml and harvested at 24 hrs and 48 hrs. The cells were lysed in 100 µl triple detergent lysis buffer, protein was precipitated by 200 µl of 10% TCA, and supernatant was washed two times with 750 µl of water saturated methyl-ter-butyl ether to remove TCA, followed by the derivatizing thiamine and its phosphate esters by using potassium ferricyanide previously described HPLC column was used. Mobile phase was A (dibasic sodium phosphate 25 mmol/L, pH 7.0: methanol) (90:10 vol/vol) and mobile phase B was (dibasic sodium phosphate 25 mmol/L, pH 7.0: methanol)(30:70 vol/vol). Gradient steps were programmed as follows: 10-15% B in 1 min, 30% B in 2 min, ramped to 50% B in 5 min, held at 50% B for 4 min, returned to initial conditions during 2 min and equilibrated for 5 min. Injection volume and detection wavelengths were the same as described above. Protein concentrations were determined by the Dc Protein Assay (Bio-Rad) and read at 750 nm. The results were adjusted for protein concentration and normalized to unincubated control specimen (pmol/mg protein). The experiment was repeated twice in duplicate.

Pharmacokinetic studies: All animal studies were approved by the University of Kentucky Institutional Animal Care and Use Committee. Pilot pharmacokinetic studies were performed with native thiaminase, and with thiaminase enzyme conjugated with 1k, 5k and 10k linear chain PEG. Using pilot data to guide time point selection, pharmacokinetic studies were performed with native thiaminase and 5k-PEGylated thiaminase. Four animals were used for each time point. The pharmacokinetics of thiaminase activity (units/ml) in plasma were modeled using WinNonlin v5.3 (Pharsight, St. Louis, Mo.). Native thiaminase was modeled using a one-compartment model with extravascular administration and lag-time, while the 5k-PEGylated formulation model did not require lag time. Weighting methods were employed as necessary for optimum fits. Model selection criteria were based on visual observation, the magnitude of residuals, and the variance associated with parameter estimation.

Immunohistochemistry: Mice were euthanized by exposure to $CO_2$ and tissues were harvested at the end of the pharmacokinetic study observation periods (at 24 hr for native thiaminase and 168 hours for 5k-PEGylated thiaminase). Tissues were fixed in 10% formalin. Tissue sections were mounted on glass slides and stained in Hematoxylin solution #3 (Fisher) followed by 1% Eosin Y solution (Fisher), then washed with ethanol and mounted. For immunohistochemical detection of thiaminase, the tissues sections were blocked in a solution of telostein gelatin and Triton X, followed by 20 min in normal blocking solution, then incubated with the primary antibody for 1 hr and the secondary biotinylated antibody for 20 min. The slides were developed with ABC reagent, washed, deparafinized and mounted.

Xenograft studies: All animal studies were approved by the University of Kentucky Institutional Animal Care and Use Committee. RS4 leukemia cells ($1 \times 10^7$) were injected subcutaneously into the flanks of 5-6 week old female Crl:NU-Foxn1 nude mice (Charles River Laboratories, Wilmington, Mass.). When palpable tumors had formed, mice were treated with native thiaminase (850 units/kg SC) twice weekly for 4 weeks (n=10) or a single dose of 5k-PEG thiaminase at its MTD (5 units/kg) (n=10) at a site distant from the formed tumor. The predetermined endpoints were a tumor volume of 1500 mm$^3$ or death. All of the events in the control and 5k-PEG thiaminase cohorts were tumor progression. In the native thiaminase cohort, one of the events was unexplained death. The control group of mice were injected with RS4 cells and left untreated, and results combined with a previous control group of the same xenograft (Daily, et al, 2011). Kaplan-Meier survival curves and statistical analysis was performed with GraphPad Prism software.

Results

Figure 17:
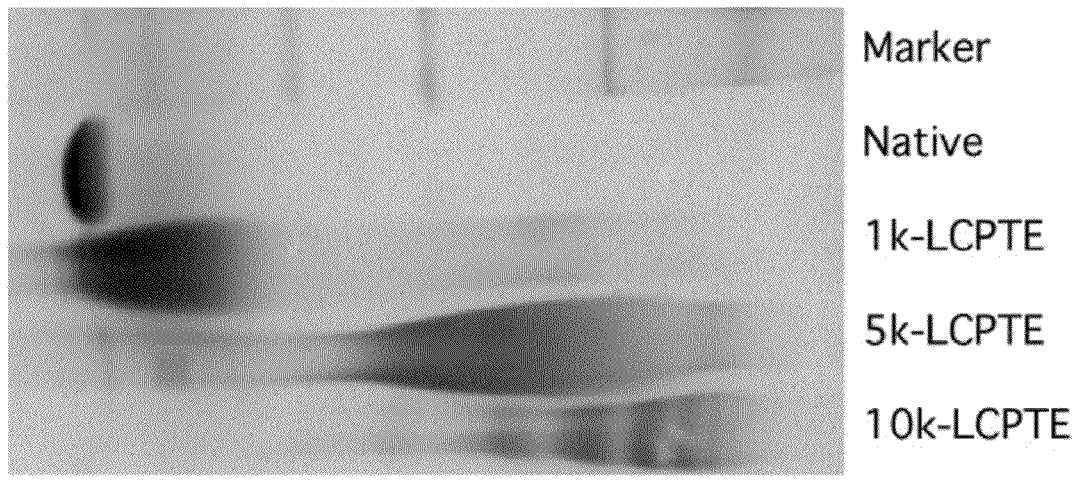
FIG. 17 is a Coomassie-stained SDS gel showing PEGylation of thiaminase I was completed using 1k, 5k and 10k linear chain polyethylene glycol.

Native thiaminase was successfully conjugated with 1k-5k- and 10k-linear chains of polyethylene glycol. As expected, PEGylation changed the particle size of the enzyme as determined by dynamic light scattering to 4.5 nm, 6.78 nm, 11.8 nm and 28.3 nm for native, 1k-, 5k-, and 10k-PEGylated forms, respectively. Consistent with the size increase, the modification decreased the mobility of the enzyme on SDS gel electrophoresis, with the longer chain modified forms showing more restricted and diffused mobility (FIG. 17).

Figure 18:
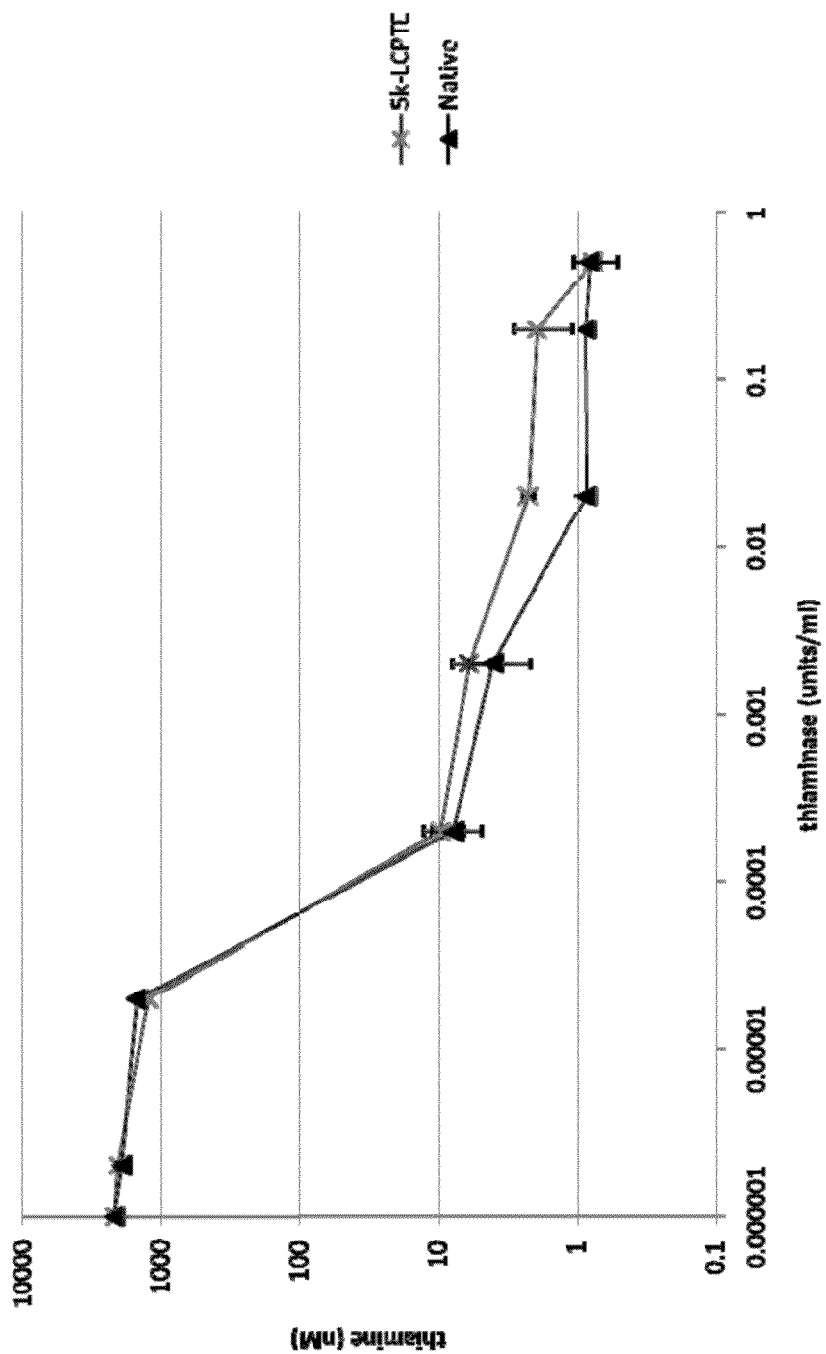
FIG. 18 includes results of a fluorescent detection HPLC detection method used to determine the concentration of thiaminase required to deplete cell culture medium of thiamine; a concentration of 0.001 units/ml depleted medium of thiamine to a level less than 10 nM after a 24 hour incubation.

The ability of native thiaminase and 5k-PEGylated thiaminase to deplete thiamine in cell culture medium is shown in FIG. 18. Medium containing 10% fetal bovine serum was incubated at 37° C. for one day, to recapitulate cell culture conditions. Both forms of the enzyme were equally as effective at reducing thiamine from 3 uM to 10 nM. However, the native enzyme was more efficient at the lower thiamine concentrations in further depletion, decreasing thiamine concentrations to less than 1 nM at a concentration of 0.02 units/ml, whereas 5k-thiaminase required a concentration of 0.5 units/ml.

Figure 19:
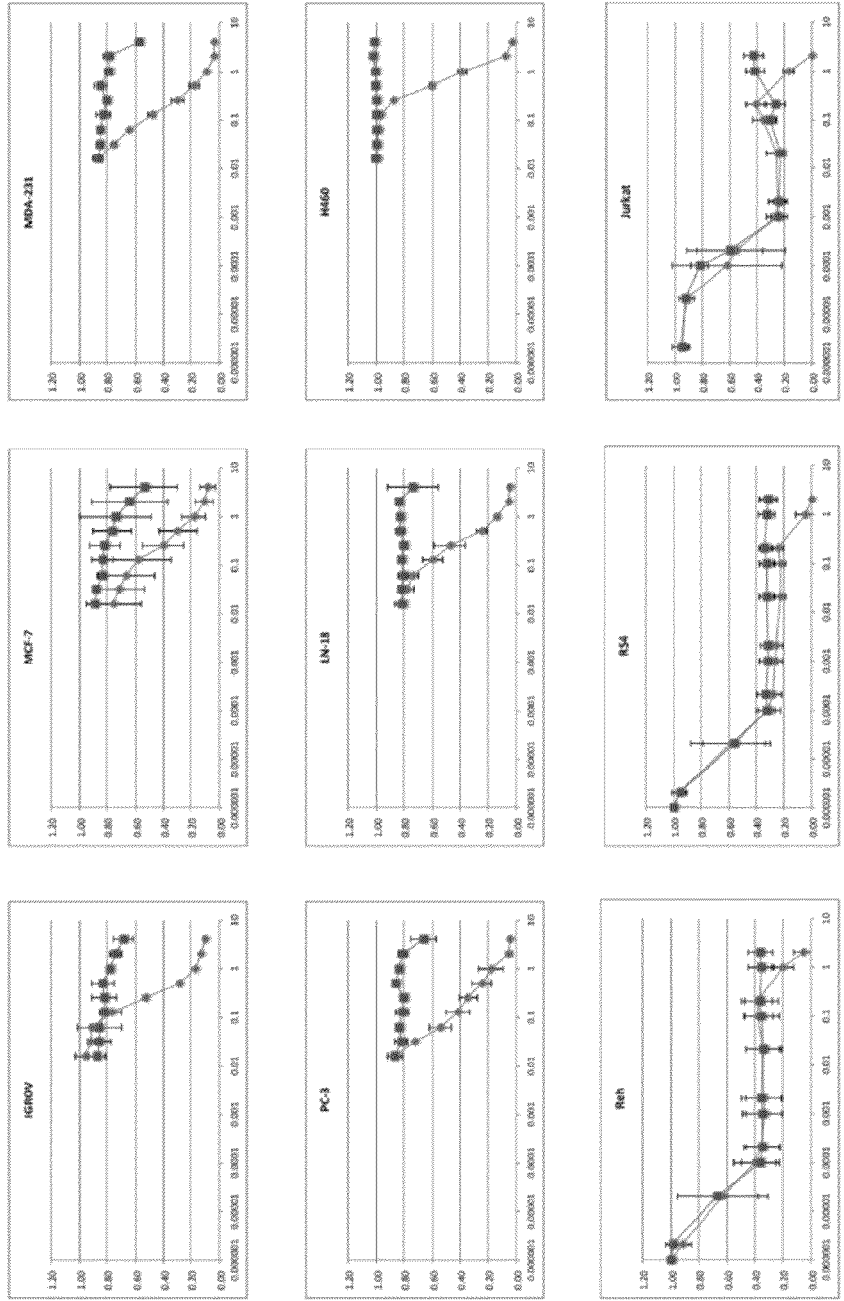
FIG. 19 is a dose response curves of 9 cancer cell lines showing growth relative to control of cells treated with increasing concentrations of native or 5k-PEGylated thiaminase enzyme.

The cytotoxic potency of native vs 5k-PEG thiamianse in 9 different cell lines is shown in FIG. 19. Surprisingly, 5k-PEG thiaminase was inert in the 6 solid tumor monolayer cell lines. In contrast, 5k-PEG thiaminase and native thiaminase were equally potent and achieved growth inhibition in Reh, RS4 and Jurkat leukemia cell lines at enzyme concentrations that depleted thiamine in the growth medium (FIG. 18). However, at higher enzyme concentrations cell killing appeared to occur with native thiaminase but not with 5k-PEG thiaminase. Notably, cytotoxicity in all cell lines occurred at native thiaminase concentrations far higher than the concentration needed to deplete medium of thiamine.

Figure 20:
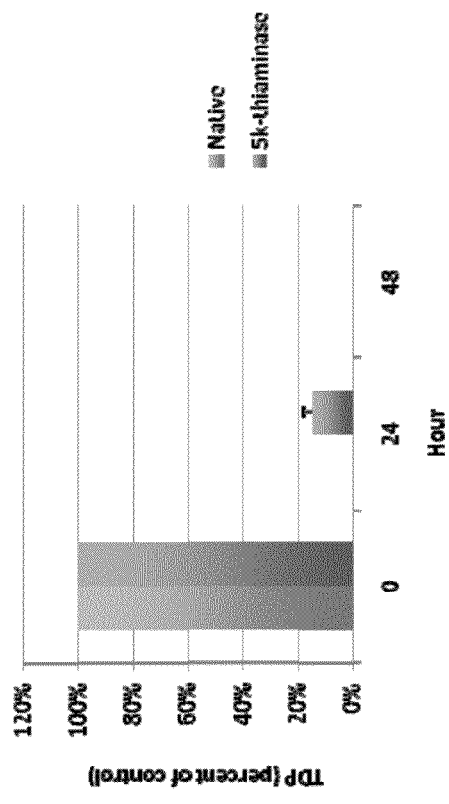
FIG. 20 includes Panels A-C and includes the following: Panel A—Thiamine monophosphate and thiamine diphosphate were substitute for thiamine as substrates and relative activity of native thiaminase and 5k-PEGylated thiaminase determined and expressed as the fraction of activity relative to thiamine as substrate; Panel B—Intracellular thiamine in RS4 leukemia cells after 24 and 48 hr incubation in native thiaminase and 5k-PEG thiaminase expressed as a percent of control; and Panel C—Intracellular thiamine diphosphate (thiamine pyrophosphate) in RS4 leukemia cells after 24 and 48 hr incubation in native thiaminase and 5k-PEG thiaminase expressed as a percent of control.
Figure 20:
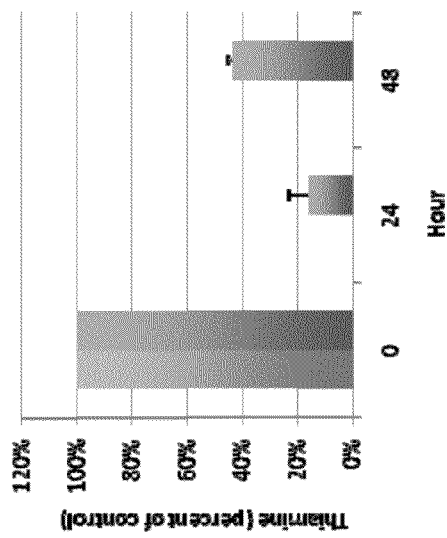

To determine whether 5k-PEGylation decreased cytotoxic effect by decreasing cellular thiamine catabolism, the present inventors first determined that native and 5-PEGylated enzymes were equally efficient at catabolizing the major forms of intracellular thiamine thiamine pyrophosphate (thiamine diphsophate) and thiamine monophosphate (FIG. 20). Both phosphorylated thiamine derivatives were determined to be substrates for both forms of the enzyme by spectrophotometric assay (panel A). Next, the present inventors examined intracellular thiamine and thiamine diphoshate (thiamine pyrophosphate) in RS4 cells exposed to equal concentrations of native thiaminase and 5k-PEGylated thiaminase, and found that native thiaminse was much more efficient at depleting both intracellular thiamine (panel B) and thiamine diphosphate (panel C) than the 5k-PEGylated form of the enzyme.

Figure 21:
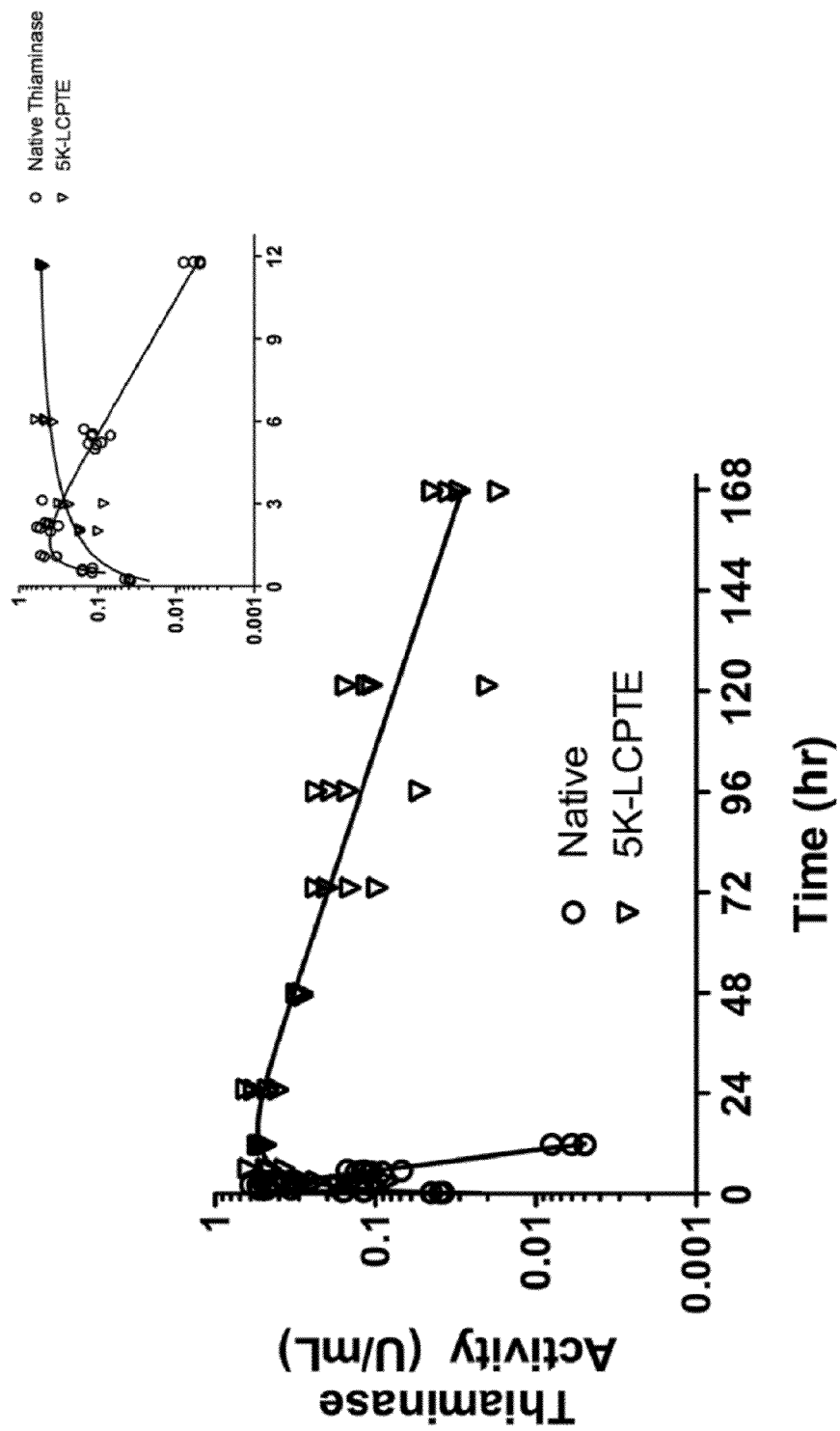
FIG. 21 includes activity-time profiles of native thiaminase and 5k-PEGylated thiaminase (5k-LCPTE) after 24 or 168 h of single dose of native thiaminase (300 U/kg) or 5k PEG thiaminase (10 U/kg). Native thiaminase was rapidly cleared in vivo, and PEGylation appears to greatly enhance the plasma retention time and in vivo potency.

FIG. 21 and Table 1 show the activity-time profiles and pharmacokinetic parameters after 24 hr or 168 hr of a single subcutaneous dose of native thiaminase (300 units/kg) or 5k-PEG thiaminase (10 U/kg). Native thiaminase was rapidly cleared in vivo, and PEGylation greatly enhanced the plasma retention time and in vivo potency. 5k-PEGylation increased the plasma retention time from 1.47 hr to 34.4 hr, an increase of 23.4-fold, and similarly increased the AUC from 1.54 hr*units/ml to 36.71 hr*units/ml. The estimated maximum concentration was similar for both the 300 units/kg of native enzyme and 10 units/kg of 5k-thiaminase, at 0.41 units/ml and 0.54 units/ml, respectively.

TABLE 1

| Parameter | Units | Estimate | StdError | CV % |
|---|---|---|---|---|
| Native thiaminase 300 units/kg SC | | | | |
| AUC | hr * U/mL | 1.54 | 0.15 | 9.98 |
| $t_{1/2}$ | hr | 1.47 | 0.14 | 9.56 |
| CL/F | mL/hr/kg | 194.8 | 19.45 | 9.99 |
| Tmax | hr | 1.63 | 0.19 | 11.42 |
| Cmax | U/mL | 0.41 | 0.06 | 15.07 |
| V/F | mL/kg | 413.86 | 64.49 | 15.58 |
| 5k-thiaminase 10 units/kg SC | | | | |
| AUC | hr * U/mL | 36.71 | 2.67 | 7.28 |
| $t_{1/2}$ | hr | 34.43 | 4.56 | 13.23 |
| CL/F | mL/hr/kg | 0.27 | 0.02 | 7.28 |
| Tmax | hr | 15.38 | 1.26 | 8.17 |
| Cmax | U/mL | 0.54 | 0.02 | 4.42 |
| V/F | mL/kg | 13.53 | 1.21 | 8.97 |

Data from pilot pharmacokinetic studies were used to estimate the exposure following administration of 1k- and 10k-PEGylated thiaminase. The dose adjusted AUCs (AUC/dose (units/kg)) are compared in Table 2. The 5k-thiaminase modification produced both the highest dose-adjusted AUC and was the most potent with respect to the maximum tolerated dose of the 3 modifications tested. This difference in the dose adjusted AUC between the 5k- and 10k-PEGylated thiaminase formulations was likely due to a difference in bioavailability. It is possible that the larger effective particle size had reduced access to plasma following its subcutaneous administration. Clearance mechanisms could also play a role in the lower exposure, although such mechanisms are typically observed with much larger particles (e.g., 50-200 nm).

TABLE 2

| | AUC/ units/kg | Relative to native | MTD (units/kg) | Relative 1/MTD |
|---|---|---|---|---|
| Native thiaminase | 0.005 | 1 | 300 × 14 | 1 |
| 1k-thiaminase* | 0.025 | 5 | 50 | 84 |
| 5k-thiaminase | 3.7 | 740 | 5 | 840 |
| 10k-thiaminase* | 0.54 | 108 | 10 | 420 |

*estimated AUC

Figure 22:
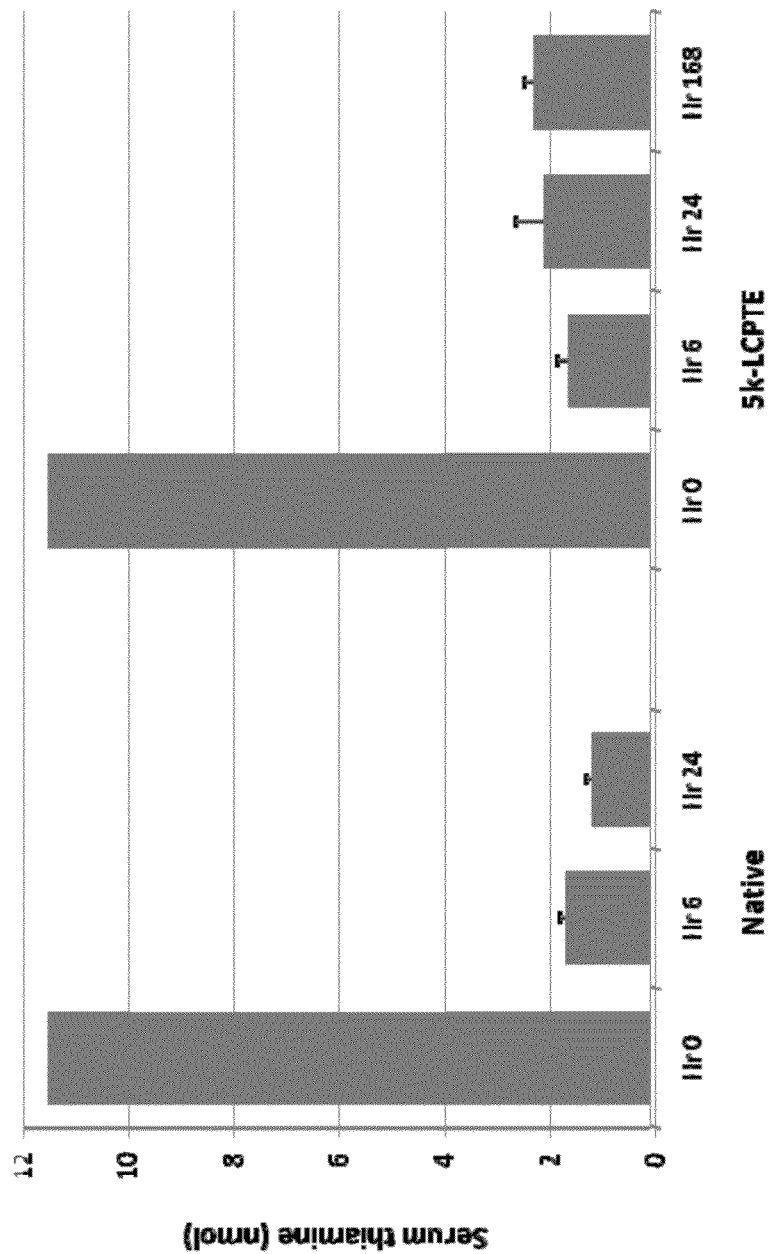
FIG. 22 shows the concentration of thiamine in mouse serum after single dose of native thiaminase (300 U/kg) or 5k-PEG thiaminase (10 U/kg) treatment. The result shows thiamine was depleted in vivo after native thiaminase or 5k-PEG thiaminase treatment within 6 hours, and lasted through the end of the pharmacokinetic experiment for 5k-PEGylated thiaminase at hour 168.

FIG. 22 shows the depletion of thiamine in serum corresponding to time points obtained for pharmacokinetic sampling, and represent the extracellular pharmacodynamic effect of thiaminase. In comparison to studies of thiamianse depletion in tissue culture medium, where the starting thiamine concentration is 3 uM, the baseline serum concentration was measured at 11 nM. Even though at 24 hours the concentration of native thiaminase was below the limit of detection, the 24 hour thiamine level was 1.7-fold lower than the 24 hour level produced by 5k-thiaminase, 1.2±0.2 vs 2.1±0.8 nmol, respectively. This result is consistent with the observation in FIG. 18 that native thiaminase may be more efficient than 5k-PEGylated thiaminase at lower thiamine concentrations. However, the single dose of 5k thiaminase maintained relative thiamine deprivation up through hour 168.

Figure 23:
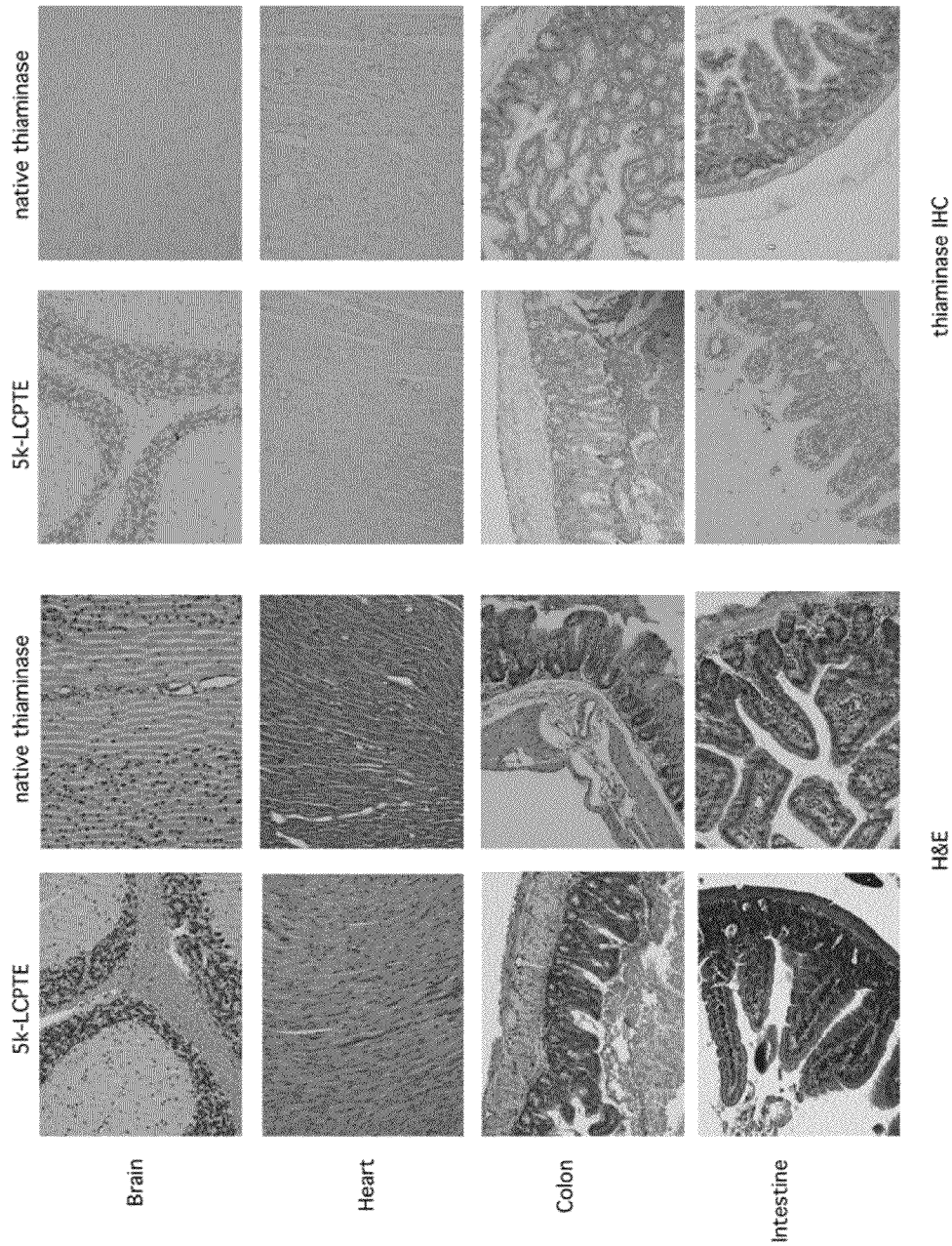
FIG. 23 includes results of a histology study using hematoxylin and eosin staining and immunohistochemistry using a polyclonal antibody against thiaminase I in tissues harvested at the end of the pharmacokinetic studies for native thiaminase (300 units/kg at 24 hours) and 5k-PEG thiaminase (10 units/kg at 168 hours); there was no evidence of heart or brain pathology or thiaminase accumulation in these tissues; there was immunohistochemical evidence of thiaminase accumulation in gastrointestinal tissues FIG. 24 includes the results of a studie in which RS4 subcutaneous xenografts were treated with 5k-PEG thiaminase and native thiaminase compared with no treatment control. Kaplan-Meier plot of event-free survival (EFS) of mice with palpable subcutaneous RS4 leukemia xenografts; the pre-determined endpoint was a tumor volume of 1500 mm$^3$ or death; for native thiaminase the median EFS post-treatment was 70 days in comparison to the EFS of 16 days for control group (p<0.001) and 14 days for the 5k-PEG thiaminase treated group, in an experiment stopped at day 100; in previously published data shown for comparison, the median EFS for 1k-PEGylated thiaminase was 31 days in the treated group (vs control p=0.03). 5 of 10 mice in the native thiaminae group showed regression of tumor by day 100 post treatment.

Lethality experiments designed to estimate the maximum tolerated dose (MTD) determined that the dose limiting toxicity of all forms of thiaminase appears to be gastrointestinal toxicity, not cardiac or central nervous system toxicity as might be expected from thiamine starvation. Tissues harvested at the end of the pharmacokinetic studies of native and 5k-PEG thiaminase are shown in FIG. 23. Tissues were stained with hematoxylin and eosin (H&E) stains and by immunohistochemistry with the polyclonal antibody raised against a thiaminase peptide used in the Western blot of FIG. 20. At the doses used, H&E staining did not show evidence of tissue damage at the end of the experimental period. In addition, there was no evidence of thiaminase in heart or brain tissues probed with the anti-thiaminase antibody. However, thiaminase staining does appear in colonic epithelium, suggesting that gastrointestinal toxicity may be the result of accumulation of enzyme in the gastrointestinal tract.

Figure 24:
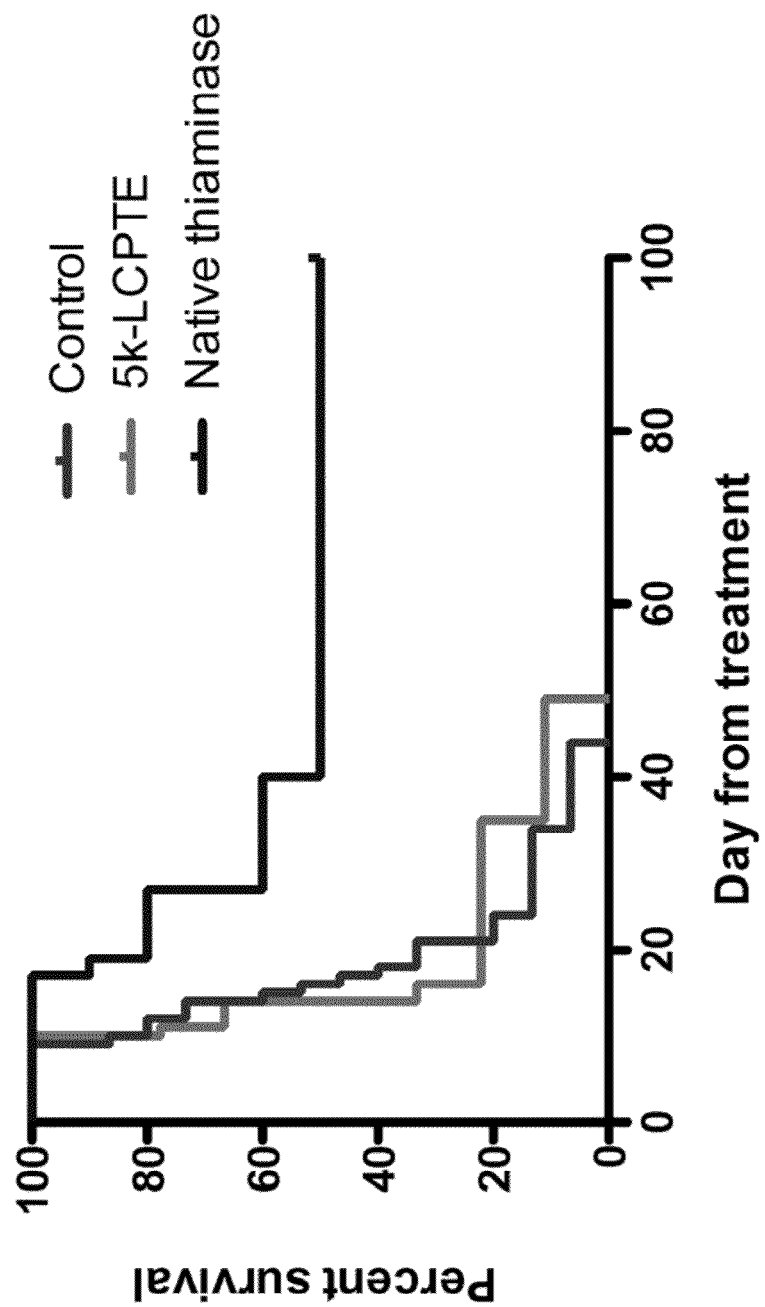

The present inventors used an established RS4 xenograft model to examine the in vivo anti-tumor activity of native and 5k-PEG thiaminases. The present inventors previously have shown that 1k-PEGylated thiaminase has activity in this model (Daily, et al., 2011). As shown in FIG. 24, 5k-PEG thiaminase has no activity compared to the control group, whereas native thiaminase increases the EFS from 15 days to 70 days (p<0.001) in an experiment that was terminated at Day 100 from the initiation of treatment. In comparison, the present inventors have previously shown that 1k-PEG thiaminase increases the EFS to 31 days (Daily, et al., 2011). Thus, at their respective MTD's, PEGylated thiaminases are not as effective as native thiaminase in this tumor model. On the other hand, native thiaminase appears to have promising activity, with not only significantly increased median EFS, but also from the observation that 5 of 10 mice with established RS4 xenografts showed tumor regression up through Day 100.

Discussion

The present inventors have explored the concept of using the bacterial enzyme thiaminase to disrupt energy metabolism in cancer. To optimize the biological and pharmacologic properties of this enzyme, the present inventors studied the effects of modifying it with the addition of linear polyethylene glycol chains of various sizes, a common technique that can increase plasma retention time and reduce immunogenicity of foreign proteins. FIG. 17 demonstrates that the protein was successfully modified by these PEG chains of various lengths. For most of the subsequent studies the present inventors focused on the intermediate, 5k-PEG modified thiaminase enzyme in comparison to native enzyme.

The present inventors initially hypothesized that thiaminase worked through an extracellular mechanism of action, by catabolizing extracellular thiamine and causing acute thiamine starvation. Indeed, FIG. 18 shows that both native and 5k-PEG thiaminase are very potent in the catabolism of thiamine, achieving a 100-fold reduction of thiamine in medium at concentrations of 0.0001 units/ml.

The comparison of the cytotoxicity profiles of native and 5k-PEG thiaminase in FIG. 19 to the concentrations needed to deplete thiamine in medium demonstrated three surprising results. First, most solid tumor cell lines showed cytotoxicity at concentrations of thiaminase (0.1-2 units/ml) that were orders of magnitude greater than the concentration needed to deplete medium of thiamine. Second, in these cell lines, 5k-PEG thiaminase was inert. Third, in leukemia cell lines, growth inhibition occurred at the enzyme concentrations that correspond with thiamine depletion for both native and 5k-PEGylated enzyme, but further cytotoxicity occurred only at the concentrations that were required for cytotoxicity in the solid tumor cell lines, and, again, 5k-PEG thiaminase did not achieve further cytotoxicity. The present inventors previously had reported the growth inhibition of thiaminase in leukemia cells at low thiaminase concentrations (Daily, et al., 2011).

These observations suggested that thiaminase did not cause cytotoxicity by extracellular thiamine depletion, but that intracellular enzyme uptake was necessary for cytotoxicity. The present inventors therefore hypothesized that native thiaminase and 5k-PEG thiaminase differed in cellular uptake. This hypothesis was supported by the studies shown in FIG. 20, where native thiaminase shows more efficient removal of both thiamine diphosphate and thiamine from the cytosol of RS4 leukemia cells.

Nevertheless, the PEG modification did have the expected effect on the pharmacokinetics of thiaminase (FIG. 21 and Table 1). 5k-PEGylated thiaminase demonstrated a significant prolongation in plasma retention time, with an increase plasma half-life of over 20-fold. Of significant interest, although 5k-PEG thiaminase did not demonstrate any appreciable toxicity in vitro against cancer cell lines, it was appreciably more toxic in vivo, with an increase in its MTD in proportion to its dose-adjusted AUC. However, at tolerable doses, native thiaminase was far more active against an RS4 leukemia xenograft than 5k-PEG thiaminase. The lack of in vitro cytotoxicity correlated with the lack of in vivo efficacy.

The dose limiting toxicity appears to be gastrointestinal; at lethal doses food accumulates in the stomach and a picture of colitis becomes apparent. The toxicity of thiaminase for native enzyme, and all PEGylated forms, appears similar. The expected toxicity in the brain and heart, the most affected organs during thiamine starvation, is not observed. Unlike cancer cells, there is evidence that 5k-PEGylated thiaminase as well as native thiaminase can accumulate in gastrointestinal cells, (FIG. 23) again suggesting that cellular uptake is required for toxicity in most cells.

Thus, although PEGylation improved the pharmacokinetic properties of the enzyme, the modification resulted in an inferior product that had less in vitro activity, more toxicity and reduced anti-tumor activity in a xenograft model. The antitumor potential of thiaminase therapy is demonstrated, as administration of the native enzyme, a completely novel therapy, resulted in a significant tumor response, with regression of established tumors, in a subcutaneous RS4 leukemia xenograft model (FIG. 24). The results point to the necessity of improving cellular uptake for cytotoxic effect, while avoiding prolonged extracellular activity that appeared to cause toxicity to normal tissues. This presents a significant challenge for the development of a protein as a therapeutic agent.

The activity of native thiaminase against cell lines and established RS4 xenografts demonstrates the therapeutic potential of this novel approach. The challenge of improving cellular uptake to enhance cellular effect has been met with other proteins that are used as therapeutic agents, most notably the development of a modified-glucosidase protein that is transported into macrophages for the treatment of Gaucher's disease (Cox, et al., 1996).

Example 8

The present inventors have found that acute extracellular thiamine starvation, by exposure to thiaminase I modified by PEGylation, does not result in cancer cell death (See EXAMPLE 7). It has been found that small molecule thiamine antagonists administered in the presence of thiamine are also not effective anticancer agents.

Without wishing to be bound by theory or mechanism, the present inventors have discovered that thiamine metabolism can be targeted by combining extracellular thiamine starvation with intracellular thiamine-dependent enzyme (TDE) antagonism.

As the present inventors contemplate, by analogy, both thiamine and folate are cofactors in critical cellular metabolic pathways. Antifolates can be effective without folate depletion because folate is always attaching and detaching from enzyme complexes, creating a situation where an antifolate with high affinity for the folate-dependent enzyme can outcompete folate for binding. However, the co-factor form of thiamine, thiamine pyrophosphate, remains attached to the enzyme throughout its catalytic cycle. Therefore, thiamine must be depleted to create a pool of apoenzyme (enzyme without attached cofactor), which can then be subject to inhibition, in order to acutely inhibit thiamine dependent metabolism.

The major TDEs that are involved in metabolism of glucose are pyruvate dehydrogenase, alpha-ketoglutarate dehydrogenase and transketolase Inhibition of each of these enzymes depends on both exhausting the supply on intracellular thiamine, to create apoenzyme forms of these TDEs, and then dosing with an enzyme inhibitor.

Because energy metabolism is widely disrupted in cancer, known as the Warburg effect, and because TDEs are involved in the pathways affected by the Warburg effect, a therapeutic window could be created by concomitant acute thiamine depletion and TDE antagonist therapy. It is contemplated that particular TDEs could be selected to optimize activity against a cancer of interest.

One example for creating a thiamine-based anti-cancer approach can involve administration of a thiaminase that has been modified to enhance cellular uptake. The present inventors have demonstrated that native thiaminase alone has therapeutic potential and can deplete intracellular thiamine. The products of intracellular thiamine catabolism, such as thiazole diphosphate, may act as TDE inhibitors. The present inventors contemplate improving the cellular uptake of the native enzyme using modifications. Examples of possible modifications of the enzyme include, but are not limited to, attaching lipophilic moieties to its structure, e.g., hydrophobic moieties, such as long carbon chains or benzene rings. Examples of possible formulations to enhance cellular uptake include, but are not limited to encapsulation of the enzyme in micelles or liposomes.

Another example for creating a thiamine-based anti-cancer approach can involve administration of thiaminase followed by administration of a TDE inhibitor. In this approach, thiaminase can be given first to deplete intracellular and extracellular thiamine, and can be followed by administration of TDE inhibitor. Depending on the schedule of administration selected by one skilled in the art, the TDE inhibitor selected would not be a thiaminase substrate, so it would not be broken down by residual circulating thiaminase enzyme. All forms of TDE's are contemplated, and it is contemplated that different TDEs can be selected to achieve activity against a spectrum of cancers. Examples of TDE inhibitors that could be used include, but are not limited to, oxythiamine, pyrithiamine, N3'pyridyl thiamine, and thiamine thiazolone. Furthermore, these TDE inhibitors can be modified to make them more lipid soluble and orally bioavailable.

Throughout this document, various references are mentioned. All such references are incorporated herein by reference, including the references set forth in the following list:

REFERENCES

1. Buzzai, M., Bauer, D. E., Jones, R. G., Deberardinis, R. J., Hatzivassiliou, G., Elstrom, R. L., and Thompson, C. B. The glucose dependence of Akt-transformed cells can be reversed by pharmacologic activation of fatty acid beta-oxidation. Oncogene, 2005.
2. Elstrom, R. L., Bauer, D. E., Buzzai, M., Karnauskas, R., Harris, M. H., Plas, D. R., Zhuang, H., Cinalli, R. M., Alavi, A., Rudin, C. M., and Thompson, C. B. Akt stimulates aerobic glycolysis in cancer cells. Cancer Res, 64: 3892-3899, 2004.
3. Liu, S., Huang, H., Lu, X., Golinski, M., Comesse, S., Watt, D., Grossman, R. B., and Moscow, J. A. Down-regulation of thiamine transporter THTR2 gene expression in breast cancer and its association with resistance to apoptosis. Mol Cancer Res, 1: 665-673, 2003.
4. Liu, S., Stromberg, A., Tai, H. H., and Moscow, J. A. Thiamine transporter gene expression and exogenous thiamine modulate the expression of genes involved in drug and prostaglandin metabolism in breast cancer cells. Mol Cancer Res, 2: 477-487, 2004.
5. Costello, C. A., Kelleher, N. L., Abe, M., McLafferty, F. W., and Begley, T. P. Mechanistic studies on thiaminase I. Overexpression and identification of the active site nucleophile. J Biol Chem, 271: 3445-3452, 1996.
6. Bettendorff, L., Goessens, G., Sluse, F., Wins, P., Bureau, M., Laschet, J., and Grisar, T. Thiamine deficiency in cultured neuroblastoma cells: effect on mitochondrial function and peripheral benzodiazepine receptors. J Neurochem, 64: 2013-2021, 1995.
7. Bettendorff, L. and Wins, P. Mechanism of thiamine transport in neuroblastoma cells. J. Biol. Chem., 269: 14379-14385, 1994.
8. Chen, G. and Waxman, D. J. Role of cellular glutathione and glutathione S-transferase in the expression of alkylating agent cytotoxicity in human breast cancer cells. Biochem Pharmacol, 47: 1079-1087, 1994.
9. Brognard, J., Clark, A. S., Ni, Y., and Dennis, P. A. Akt/protein kinase B is constitutively active in non-small cell lung cancer cells and promotes cellular survival and resistance to chemotherapy and radiation. Cancer Res, 61: 3986-3997, 2001.
10. Kraus, A. C., Ferber, I., Bachmann, S. O., Specht, H., Wimmel, A., Gross, M. W., Schlegel, J., Suske, G., and Schuermann, M. In vitro chemo- and radio-resistance in small cell lung cancer correlates with cell adhesion and constitutive activation of AKT and MAP kinase pathways. Oncogene, 21: 8683-8695, 2002.
11. Krystal, G. W., Sulanke, G., and Litz, J. Inhibition of phosphatidylinositol 3-kinase-Akt signaling blocks growth, promotes apoptosis, and enhances sensitivity of small cell lung cancer cells to chemotherapy. Mol Cancer Ther, 1: 913-922, 2002.
12. Koizumi, N., Hatano, E., Nitta, T., Tada, M., Harada, N., Taura, K., Ikai, I., and Shimahara, Y. Blocking of PI3K/Akt pathway enhances apoptosis induced by SN-38, an active form of CPT-11, in human hepatoma cells. Int J Oncol, 26: 1301-1306, 2005.
13. Monks, N., Liu, S., Xu, Y., Yu, H., Bendelow, A., and Moscow, J. Potent cytotoxicity of the phosphatase inhibitor microcystin LR and microcystin analogues in OATP1B1- and OATP1B3-expressing HeLa cells. Molecular Cancer Therapeutics, 6: 587-598, 2007.
14. Campobasso, N., Costello, C. A., Kinsland, C., Begley, T. P., and Ealick, S. E. Crystal structure of thiaminase-I from *Bacillus thiaminolyticus* at 2.0 A resolution. Biochemistry, 37: 15981-15989, 1998.
15. Nishimune, T., Watanabe, Y., and Okazaki, H. Studies on the polymorphism of thiaminase I in seawater fish. J Nutr Sci Vitaminol (Tokyo), 54: 339-346, 2008.

16. Thomas, K. W. The effect of thiaminase-induced subclinical thiamine deficiency on growth of weaner sheep. Vet Res Commun, 10: 125-141, 1986.
17. Davenport, E. L., Morgan, G. J., and Davies, F. E. Untangling the unfolded protein response. Cell Cycle, 7: 865-869, 2008.
18. Lee, A. S. GRP78 induction in cancer: therapeutic and prognostic implications. Cancer Res, 67: 3496-3499, 2007.
19. Li, J. and Lee, A. S. Stress induction of GRP78/BiP and its role in cancer. Curr Mol Med, 6: 45-54, 2006.
20. Jamora, C., Dennert, G., and Lee, A. S. Inhibition of tumor progression by suppression of stress protein GRP78/BiP induction in fibrosarcoma B/C10ME. Proc Natl Acad Sci USA, 93: 7690-7694, 1996.
21. Vander Heiden M G, Cantley L C, Thompson C B. Understanding the Warburg effect: the metabolic requirements of cell proliferation. Science 2009; 324: 1029-33.
22. Garber K. Energy boost: the Warburg effect returns in a new theory of cancer. J Natl Cancer Inst 2004; 96: 1805-6.
23. Roberts M J, Bentley M D, Harris J M. Chemistry for peptide and protein PEGylation. Adv Drug Deliv Rev 2002; 54: 459-76.
24. Richardson A D, Yang C, Osterman A, Smith J W. Central carbon metabolism in the progression of mammary carcinoma. Breast Cancer Res Treat 2008; 110: 297-307.
25. Cox T M (2010) Gaucher disease: clinical profile and therapeutic developments. Biologics: targets & therapy 4: 299-313
26. Daily A, Liu S, Bae Y, Bhatnagar S, Moscow J A (2011) Linear Chain PEGylated Recombinant *Bacillus Thiaminolyticus* Thiaminase I Enzyme Has Growth Inhibitory Activity against Lymphoid Leukemia Cell Lines. Mol Cancer Ther 10: 1563-70
27. Gangolf M, Czerniecki J, Radermecker M, Detry O, Nisolle M, Jouan C, Martin D, Chantraine F, Lakaye B, Wins P, Grisar T, Bettendorff L (2010) Thiamine status in humans and content of phosphorylated thiamine derivatives in biopsies and cultured cells. PLoS One 5: e13616
28. Hanes J W, Kraft C E, Begley T P (2007) An assay for thiaminase I in complex biological samples. Anal Biochem 368: 33-8
29. Liu S, Monks N R, Hanes J W, Begley T P, Yu H, Moscow J A (2010) Sensitivity of breast cancer cell lines to recombinant thiaminase I. Cancer Chemother Pharmacol 66: 171-9
30. Lu J, Frank E L (2008) Rapid HPLC measurement of thiamine and its phosphate esters in whole blood. Clinical chemistry 54: 901-6
31. Richardson A D, Moscow J A (2010) Can an enzyme cofactor be a factor in malignant progression? Cancer Biol Ther 10: 32-34
32. Steinhauer J, Treisman J E. Lipid-modified morphogens: Functions of fats. Current Opinion in Genetics & Development. 2009; 19(4):308-14.
33. Miura G I, Treisman J E. Lipid modification of secreted signaling proteins. Cell Cycle. 2006; 5(11):1184-8.
34. Porter J A, Ekker S C, Park W J, vonKessler D P, Young K E, Chen C H, et al. Hedgehog patterning activity: Role of a lipophilic modification mediated by the carboxy-terminal autoprocessing domain. Cell. 1996; 86(1):21-34.
35. Mueller G. Oral Protein Therapy for the Future—Transport of Glycolipid-Modified Proteins: Vision or Fiction? Pharmacology. 2010; 86(2):92-116.
36. Wadher K, Kalsait R, Umekar M. Oral insulin delivery: facts, developments and challenges. Pharmacia Lettre. 2009; 1(2):121-9.
37. Morishita M, Peppas N A. Is the oral route possible for peptide and protein drug delivery? Drug Discovery Today. 2006; 11(19 & 20):905-10.
38. Gauthier M A, Klok H-A. Polymer-protein conjugates: an enzymatic activity perspective. Polymer Chemistry. 2010; 1(9):1352-73.
39. Bernardes G J L, Chalker J M, Davis B G. Chemical protein modification. Ideas in Chemistry and Molecular Sciences: Where Chemistry Meets Life. 2010:59-91.
40. Lee Y, Fukushima S, Bae Y, Hiki S, Ishii T, Kataoka K. A Protein Nanocarrier from Charge-Conversion Polymer in Response to Endosomal pH. Journal of the American Chemical Society. 2007; 129(17):5362-3.
41. Diezi T A, Bae Y, Kwon G S. Enhanced Stability of PEG-block-poly(N-hexyl stearate L-aspartamide) Micelles in the Presence of Serum Proteins. Molecular Pharmaceutics. 2010; 7(4):1355-60.
42. Huerou Y L, Gunawardana I, Thomas A A, Boyd S A, deMeese J, deWolf W, Gonzales S S, Han M, Hayter L, Kaplan T, Lemieux C, Lee P, Pheneger J, Poch G, Romoff T T, Sullivan F, Weiler S, Wright S K, Lin J. Prodrug thiamine analogs as inhibitors of the enzyme transketolase. Bioorganic & Medicinal Chemistry Letters. 2007; 18:505-508.
43. Thomas A A, Huerou Y L, DeMeese J, Gunawardana I, Kaplan T, Romoff T T, Gonzales Ss, Condroski K, Boyd S A, Ballard J, Bernat B, DeWolf W, Han M, Lee P, Lemieux C, Pedersen R, Pheneger J, Pock G, Smith D, Sullivan F, Swiler S, Wright S K, Lin J, Brandhuber B, Vigers G. Synthesis in vitro and in vivo activity of thiamine antagonist transketolase inhibitors. Bioorganic & Medicinal Chemistry Letters. 2008; 18:2206-2210.

What is claimed is:

1. A method for treating cancer, comprising: administering to a subject in need thereof an effective amount of a thiaminase compound, and administering to the subject an effective amount of a thiaminase substrate, wherein the thiaminase substrate is thiamine.

2. The method of claim 1, wherein the thiaminase compound is a thiaminase enzyme modified with a lipophilic moiety.

3. The method of claim 1, wherein the thiaminase compound is a thiaminase enzyme encapsulated in a lipophilic carrier.

4. The method of claim 1, wherein the thiaminase compound is a thiaminase enzyme.

5. The method of claim 4, wherein the thiaminase enzyme has the amino acid sequence of a native thiaminase I or a native thiaminase II.

6. The method of claim 5, wherein the native thiaminase I is from *Bacillus thiamineolyticus*.

7. The method of claim 1, and further comprising administration of an anti-cancer agent and/or radiation.

8. The method of claim 1, wherein the thiaminase compound is administered subcutaneously, intramuscularly, or intravenously.

9. The method of claim 1, wherein the thiaminase compound is administered prior to administration of the TDE inhibitor.

10. The method of claim 1, wherein administration of the thiaminase compound in combination with the TDE inhibitor produces a synergistic effect.

* * * * *